(12) United States Patent
Van Der Zande et al.

(10) Patent No.: US 9,049,882 B2
(45) Date of Patent: Jun. 9, 2015

(54) WHEY PROTEIN COMPOSITION WITH A REDUCED ASTRINGENCY

(75) Inventors: Matthijs Leonard Joseph Van Der Zande, Wageningen (NL); Gerrit Jan Waterink, Wageningen (NL)

(73) Assignee: N.V. Nutricia (NL)

( * ) Notice: Subject to any disclaimer, the term of this patent is extended or adjusted under 35 U.S.C. 154(b) by 0 days.

(21) Appl. No.: 13/994,222

(22) PCT Filed: Dec. 16, 2011

(86) PCT No.: PCT/NL2011/050857
§ 371 (c)(1),
(2), (4) Date: Sep. 17, 2013

(87) PCT Pub. No.: WO2012/081982
PCT Pub. Date: Jun. 21, 2012

(65) Prior Publication Data
US 2014/0296162 A1    Oct. 2, 2014

(30) Foreign Application Priority Data

Dec. 17, 2010  (WO) ................ PCT/NL2010/050866

(51) Int. Cl.
| | | |
|---|---|---|
| *A61K 38/11* | (2006.01) | |
| *A23L 1/29* | (2006.01) | |
| *A23J 3/08* | (2006.01) | |
| *A23J 3/16* | (2006.01) | |
| *A23L 1/30* | (2006.01) | |
| *A23L 1/304* | (2006.01) | |
| *A23L 1/305* | (2006.01) | |
| *A61K 35/20* | (2006.01) | |
| *A61K 38/16* | (2006.01) | |
| *A61K 38/01* | (2006.01) | |

(52) U.S. Cl.
CPC .. *A23L 1/296* (2013.01); *A23J 3/08* (2013.01); *A23J 3/16* (2013.01); *A23L 1/3006* (2013.01); *A23L 1/304* (2013.01); *A23L 1/305* (2013.01); *A23L 1/3051* (2013.01); *A23L 1/3055* (2013.01); *A23L 1/3056* (2013.01); *A23V 2002/00* (2013.01); *A23V 2250/70* (2013.01); *A61K 35/20* (2013.01); *A23L 1/293* (2013.01); *A61K 38/168* (2013.01); *A61K 38/011* (2013.01); *A61K 38/018* (2013.01)

(58) Field of Classification Search
None
See application file for complete search history.

(56) References Cited

U.S. PATENT DOCUMENTS

| | | |
|---|---|---|
| 2009/0143301 A1 | 6/2009 | Olson et al. |
| 2011/0021421 A1 | 1/2011 | Kiers et al. |

FOREIGN PATENT DOCUMENTS

| | | | | |
|---|---|---|---|---|
| CN | 101437410 A | | 5/2009 | |
| CN | 101909468 A | | 12/2010 | |
| WO | WO 2007/108827 | * | 9/2007 | ................ A23L 1/28 |
| WO | 2009112036 A2 | | 9/2009 | |
| WO | WO 2009/113845 | * | 9/2009 | ................ A23L 1/29 |

OTHER PUBLICATIONS

Office Action issued for corresponding Chinese Patent Application No. 201180067438.6, dated May 16, 2014.
English Translation of Office Action issued for corresponding Chinese Patent Application No. 201180067438.6, dated May 16, 2014.

* cited by examiner

*Primary Examiner* — Karlheinz R Skowronek
*Assistant Examiner* — Mindy Newman
(74) *Attorney, Agent, or Firm* — Banner & Witcoff, Ltd.

(57) ABSTRACT

The invention relates to a sterilized liquid or semi-solid acid enteral composition comprising per 100 ml 9 to 20 g of non-hydrolyzed globular proteins, fat and at least 100 mg of divalent metal cations and having a pH ranging between 3 and 5. The invention further relates to a method for preparing a composition according to the invention, comprising a step wherein at least the non-hydrolyzed globular proteins are subjected to a direct steam injection (DSI) at specific holding values, such as a holding temperature of 100 to 140° C. during a holding time of about 0.5 to 10 seconds, followed by a homogenization step and a sterilization step The composition according to the invention has a reduced astringency and can be used for medical purposes, such as for stimulating muscle protein synthesis in a mammal, in particular for treating sarcopenia, and for specific groups of people, such as elderly and sportsman.

24 Claims, 1 Drawing Sheet

UHT versus DSI operating window
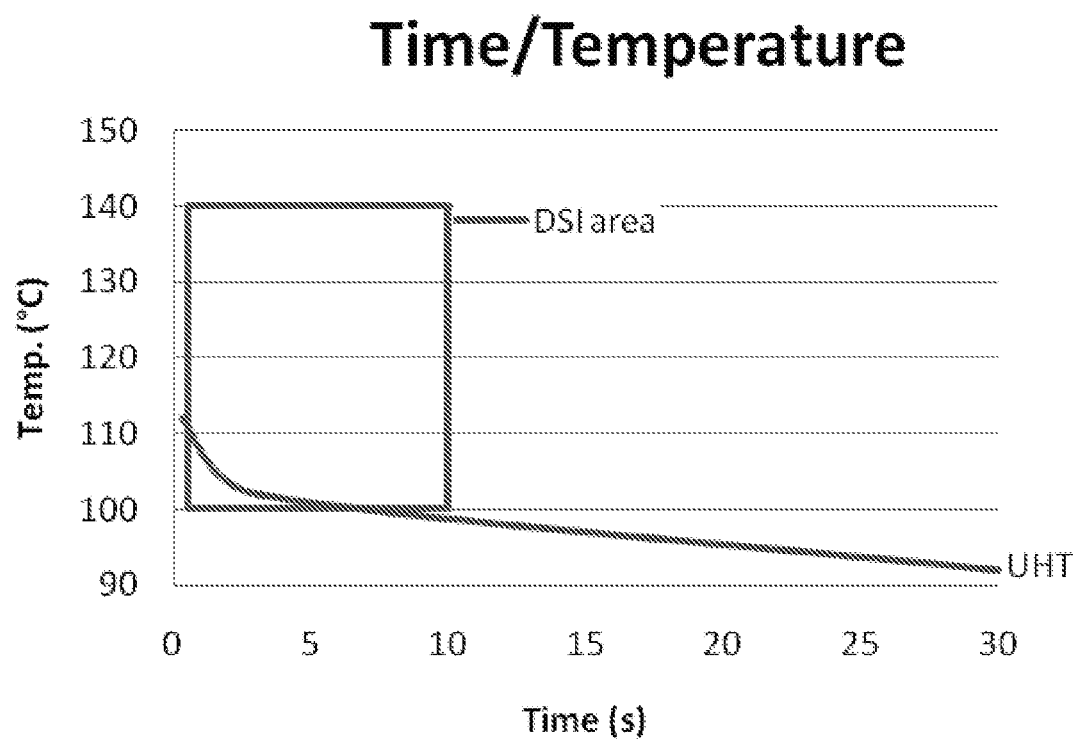

WHEY PROTEIN COMPOSITION WITH A REDUCED ASTRINGENCY

RELATED APPLICATION DATA

This application is a National Stage Application under 35 U.S.C. 371 of co-pending PCT application PCT/NL2011/050857 designating the United States and filed Dec. 16, 2011; which claims the benefit of PCT application PCT/US2010/050866 and filed Dec. 17, 2010 each of which are hereby incorporated by reference in their entireties.

FIELD OF THE INVENTION

The present invention relates to a sterilized liquid or semi-solid acid enteral composition comprising a high amount of non-hydrolysed globular proteins, such as whey, fat, and a high amount of divalent metal cations, such as calcium and magnesium, and having a reduced astringency, methods for the preparation of such composition and use of such composition in the manufacture of a nutritional food, to be used as a complete food or as a nutritional supplement. The present invention further relates to a nutritional composition useful for medical purposes, such as for stimulating muscle protein synthesis in an mammal, in particular for treating sarcopenia, and for specific groups of people, such as elderly and sportsman.

BACKGROUND OF THE INVENTION

Some subjects need nutrition, either as a supplement, or as a complete nutrition, in the smallest volume of liquid, that is still effective for its intended purpose.

These subjects can be cachectic patients or persons suffering from end-stage AIDS, cancer or cancer treatment, severe pulmonary diseases like COPD (chronic obstructive pulmonary disease), tuberculosis and other infection diseases or persons that experienced severe surgery or trauma like burns. Furthermore, persons suffering from disorders in the throat or mouth such as oesophageal cancer or stomatitis and persons having problems with swallowing like dysphagic persons, require special liquid, low-volume nutrition. Also, persons just suffering from reduced appetite or loss of taste, will benefit from low-volume, preferably liquid, food.

These subjects can also be elderly persons, in particular frail elderly and elderly at risk of becoming frail. In this regard, although an elderly person's energy needs may be reduced, their ability to consume products may also be diminished. For example, they may have difficulty consuming a product due to, e.g., swallowing difficulties, or due the too large amount of product they need to consume to meet the daily intake of nutrients. Hence, compliance is not optimal, and often, the intake is suboptimal, leading to suboptimal nourishment, and in the end, to malnutrition.

These subjects can also be sportsmen (male or female), as a sportsman also may benefit from a concentrated protein drink.

Due to a prerequisite of at least six months of shelf life in general, preferably at least 12 months, whey protein compositions need to undergo some sort of sterilization treatment in order to reduce the number of or remove possible pathogens, for instance spores, bacteria and other microorganisms, which cause spoilage of the protein composition, preferably by using heat (sterilization, pasteurization), radiation (UV-treatment), or filtration methods (ultrafiltration, diafiltration, nanofiltration). Preferred sterilization treatments include heat treatments at high temperatures for a short period, such as using a UHT (Ultra High Temperature) treatment. However, when subjecting whey proteins to heat, whey proteins are rapidly denaturated whereby the whey protein globular structure enfolds, and at a pH between 3 and 7 may form agglomerates and macrostructures, which are visible as a haze or turbidity. Eventually, the agglomerates will sediment and the nutritional composition will become unacceptable for further consumption. The use of acid whey (i.e. whey with a pH<7, preferably with a pH between 3 and 5), either obtained from an acid whey process (also known as "sour whey"), or by acidification of whey (acidified whey), obtained from acidifying sour whey or sweet whey by e.g. the addition of an acid such as phosphoric acid, is preferred because acid whey is less prone to pathogens and hence, only needs a mild sterilization treatment by heat, such as a pasteurization or UHT treatment. Furthermore, an acid whey protein composition has a more preferred taste and smell than a neutral (pH about 7) whey protein composition.

The aforementioned groups of subjects may be sensitive to food consistency and to the organoleptic properties of an acid composition comprising a high amount of non-hydrolysed globular proteins, such as whey proteins, such as, for instance viscosity, taste, smell, colour and mouth feel, in particular astringency.

Acid whey protein solutions elicit an astringent taste sensation in the mouth, irrespective of the source of whey (WPI, WPC and others). Although the exact mechanism of astringency by whey proteins is not known, it has been published (*Astringency of Bovine Milk Whey Protein*, H. Sano, T. Egashira, Y. Kinekawa, and N. Kitabatake, J. Dairy Sci. 88:2312-2317) that most of the whey protein precipitates in the mouth at about pH 5. When an acid WPI solution (pH 3.5) is placed in the oral cavity, the acid solution is mixed with saliva (pH of about 7), causing the pH of the whey protein solution to increase but to remain at a pH<5. At this pH (near the isoelectric point of the whey protein), whey protein would precipitate in the mouth. This precipitate is formed in the oral cavity and would induce astringency in a similar way to the complex precipitation formed by salivary protein and polyphenolic compounds, as can be found in wine, green tea and some fruits.

Furthermore, it was established that astringency increases with increasing whey concentrations and shows a maximum at pH 3. This makes astringency to become a real taste problem in nutritional compositions having a high amount of whey and an acidic pH. The problem is in particular apparent at an acid pH of about 3, in particular at a pH between 3 and 5.

It is further contemplated that the presence of divalent metal cations, such as magnesium and calcium—both important nutrients—may contribute to astringency. Further, it is contemplated that the presence of divalent metal cations, in particular calcium may adversely affect the solubility of whey protein and/or adversely affect viscosity of a liquid comprising whey protein, and/or adversely affect the shelf life, in particular in case the whey protein concentration is relatively high, or the liquid is heat-treated.

In view of expected problems with respect to organoleptic properties, in particular astringency, protein solubility and/or controlling viscosity, the skilled person would therefore not consider to provide a sterilized liquid or semi-solid acid enteral composition comprising a high amount of non-hydrolysed globular proteins, such as whey, fat, and a high amount of divalent metal cation, as he would not expect to be able to provide such as product with satisfactory properties for the consumer.

Therefore, a problem underlying the present invention is how to provide a sterilized liquid or semi-solid acid enteral composition comprising a high amount of non-hydrolysed globular proteins, such as whey, fat, and a high amount of divalent metal cations, such as calcium and magnesium, and having satisfactory properties, in particular satisfactory shelf life and satisfactory organoleptic properties, for providing nutrition, either as a supplement, or as a complete nutrition.

In particular, a problem underlying the invention is how to provide such a product with a satisfactory shelf life and no or a low astringency and/or no or a low sandiness More in particular, a problem underlying the invention is how to provide a sterilized liquid or semi-solid acid enteral composition comprising a high amount of non-hydrolysed globular proteins, such as whey, fat, and a high amount of divalent metal cation in a relatively small volume of liquid, whilst supporting nutrition and well-being in the different subject groups mentioned above.

The inventors have now found that such a problem is solved by preparing a sterilized liquid or semi-solid acid enteral composition in a specific way, namely using a method for producing said composition, comprising at least a direct steam injection (DSI) step, whereby the DSI is used for non-sterilizing purposes. Thus, the present invention makes it possible to provide the specific composition as defined herein below and in the claims, as an industrially applicable composition.

PRIOR ART FOR THE INVENTION

Major technical difficulties exist in producing a sterilized liquid or semi-solid acid enteral composition comprising a high amount of non-hydrolysed globular proteins, such as whey, fat, and a high amount of divalent metal cations, such as calcium and magnesium, and having a reduced astringency.

EP 1 894 477 A1 (Nestec S. A., 5 May 2008) discloses the formation of a coated denaturated supramolecular protein core structure (a liposome-like structure) comprising a whey protein aggregate and a lipidic bilayer (sulfated butyl oleate) for reduction of the astringency of protein supramolecular structures (in particular micelles).

JP 57189657 A (Mitsubishi, 22 Nov. 1982) discloses a soya milk drink, free of astringency, by adding a fatty acid ester to soya milk, homogenizing the mixture, and heat treating at 70° C.

WO 2009/112036 (Arta Foods, 17 Sep. 2009) discloses whey protein beverages with a reduced astringency comprising 0.5-15 weight % of whey and a shielding agent, in particular a monoglyceride.

WO 2007/108827 (Novartis, 27 Sep. 2007) discloses the use of DSI for reducing the viscosity of a milk protein isolate composition.

Nutritional compositions with a high amount of non-hydrolysed globular protein, in particular whey, have been described, e.g. in WO 2009/113858 (NV Nutricia, 17 Sep. 2009), in WO 2009/072884 (Nutricia, 11 Jun. 2009).

WO 2010/043415 (Nestec SA, 22 Apr. 2010) discloses a shelf-stable acid whey composition comprising 10.67 g/100 g of WPI and 5.64 g/100 g of WPH (hydrolysate)—Example 3. DSI is used as a sterilization treatment (120° C./11 sec, flash 80° C.). It is not mentioned to include divalent metal cations. The presence of a whey hydrolysate gives the resulting composition a bad taste.

SUMMARY OF THE INVENTION

The inventors have now established that a sterilized liquid or semi-solid acid enteral composition comprising a high amount of non-hydrolysed globular proteins, such as whey, fat, and a high amount of divalent metal cations, such as calcium and magnesium, and having satisfactory organoleptic properties, in particular a reduced astringency, is obtained using a process which includes a step wherein a composition is subjected to a direct steam injection (DSI) step at specific holding values and in a specific combination with other process steps, in particular after the step of homogenisation said composition and before a final sterilization treatment (meaning either sterilization or pasteurization). In a preferred embodiment, the invention provides a sterilized liquid or semi-solid acid enteral nutritional composition comprising per 100 ml of the composition 9 to 20 g of non-hydrolysed globular protein, fat, and at least 100 mg of divalent metal cations, having a pH ranging between 3 and 5, preferably ranging between about 3.7 and about 4.3, more preferably a pH of about 3.8, about 3.9, about 4.0, about 4.1 or about 4.2, most preferably a pH of about 4.0." In an advantageous embodiment, such a composition is highly appreciated because of its low astringency or the absence of astringency and/or because of its low sandiness or absence of sandiness.

In a further embodiment, the invention provides a sterilized liquid or semi-solid acid enteral nutritional composition according to the invention further comprising one or more of carbohydrates and dietary fibres. Such a composition is useful and applicable for medical purposes, such as for sarcopenia, and for specific groups of people, such as elderly and sportsman.

In a further embodiment, the invention provides the use of said sterilized liquid or semi-solid acid enteral nutritional composition according to the invention for the manufacture of a nutritional composition for providing nutrition to a person in need thereof.

In a further embodiment, the invention provides a method for the preparation of a sterilized liquid or semi-solid acid enteral composition comprising per 100 ml of said composition 9 to 20 g of non-hydrolysed globular proteins, fat, and at least 100 mg of divalent metal cations and having a pH ranging between 3 and 5, comprising a step wherein at least the non-hydrolysed globular proteins are subjected to a direct steam injection (DSI) at specific holding values, such as a holding temperature of 100 to 140° C. during a holding time of about 0.5 to 10 seconds, preceded by a homogenization step. Such a method is a valuable process tool in obtaining whey-based compositions comprising per 100 ml of said composition a high whey concentration, in particular between 9 and 20 g, fat and divalent metal cations.

In a further embodiment, the invention provides a method for the preparation of a sterilized liquid or semi-solid acid enteral composition according to the invention, comprising the consecutive steps of:

a) preparing an aqueous solution comprising amounts of divalent metal cations, in particular calcium and magnesium, non-hydrolysed globular proteins and fat, such that said sterilized liquid or semi-solid acid enteral composition comprises per 100 ml of said composition 9 to 20 g of non-hydrolysed globular proteins, fat and at least 100 mg of divalent metal cations, and having a pH ranging between 3 and 5;

b) homogenizing the resulting solution essentially obtained by step a); and c) subjecting the resulting solution essentially obtained by step b) to a direct steam injection process at a holding temperature of 100 to 140° C. during a holding time of about 0.5 to 10 seconds.

In a further embodiment the invention provides a liquid or semi-solid acid enteral nutritional composition obtained or obtainable by a method according to the invention. Such a product is in particular characterized by a relatively low astringency and/or sandiness, compared to a product having a comparative ingredient composition that has been obtained using a conventional technique or in a method wherein DSI is performed prior to homogenization.

DETAILED DESCRIPTION OF THE INVENTION

Definitions

Within the context of the present invention, an elderly person is a person of the age of 50 or more, in particular of the age of 55 or more, more in particular of the age of 60 or more, more in particular of the age of 65 or more. This rather broad definition takes into account the fact that the average age varies between different populations, on different continents, etc. Most developed world countries have accepted the chronological age of 65 years as a definition of 'elderly' or older person (associated with the age at which one may begin to receive pension benefits), but like many westernized concepts, this does not adapt well to e.g. the situation in Africa. At the moment, there is no United Nations (UN) standard numerical criterion, but the UN agreed cut-off is 60+ years to refer to the older population in Western world. The more traditional African definitions of an elder or 'elderly' person correlate with the chronological ages of 50 to 65 years, depending on the setting, the region and the country.

Within the context of the present invention, enteral means any form of administration that involves any part of the gastrointestinal tract, i.e. by mouth (orally), by gastric feeding tube, duodenal feeding tube, or gastrostomy, and rectally, in particular by mouth (orally). Hence, when referring to an enteral composition, this means that the composition is suitable for enteral administration.

Within the context of the present invention, the term "astringency" is used for a puckering or mouth drying sensation, which appears after a while in the mouth cavity after the consumption of a food. This sensation "astringency" is also characterized by terms such as rough, dry, mouth coating, or filmy mouth-feel, suggesting finely divided insoluble particles in the mouth after consumption of a food. Hence, astringency is not a taste, but a physical mouth-feeling and time depended feeling in the mouth cavity. In the same sense the term "non-astringent" is used, i.e. when no puckering or mouth drying sensation is observed in the mouth cavity when consuming a food product, such as by a trained tasting panel, in a test procedure such as the following. The "astringency value" may, as described in the Examples below, be determined or measured by a trained tasting panel following conventional specific sensory methods or by the analytical method such as the "Saliva-Beverage Interaction test" as described WO 2009/112036. In the context of the present invention, the term "reduced astringency" is used to denote an astringence which is reduced, possibly to complete absence of a noticeable astringency, in comparison to an acid composition comprising non-hydrolysed globular proteins, such as whey, having a high amount of protein and a high amount of calcium, but produced with a method according to the state of the art.

The term "sandiness" also refers to a sensory property of a liquid or semi-solid composition and typically relates to the presence of grains which causes an extraneous feeling remaining on the tongue as a distinct aftertaste. This property can be considered as an opposite to 'smoothness' or 'smooth mouth feel' and is an important factor in the acceptance of liquid as well as semi-solid compositions.

Within the context of the present invention, the term "sterilization treatment" and the term "sterilization" is meant to comprise any method using heat (sterilization, pasteurization), radiation (UV-treatment), and/or filtration (ultrafiltration, diafiltration, nanofiltration) to reduce the number of or remove possible pathogens. Preferably, the sterilization treatment includes a heat treatment at a high temperature for a short period, such as a UHT (Ultra High Temperature) treatment. Hence, within the context of the present invention, pasteurization is comprised within sterilization.

Within the context of the present invention, a "sterilized composition" is a composition that is obtained or obtainable by subjecting a composition to a sterilization treatment. In general, the quantity of potentially pathogenic micro-organisms of the sterilized composition meets food safety requirements, as applicable e.g. in the US or EU. In particular, a sterilized composition in accordance with the invention maintains to meet such requirement, for at least 6 months, preferably at least 12 months, when stored in a sealed packaging at ambient temperature (20° C.).

Within the context of the invention, the pH is the pH as measurable with a pH electrode, calibrated at pH 4 and pH 7, at a temperature of 20° C.

Within the context of the invention, the viscosity is the viscosity as measurable using an Anton Paar Physica MCR301 rheometer with a CP50-1/PC cone (diameter 50 mm, 1° difference between middle and outside) at 20° C. at 100 s$^{-1}$.

Within the context of the invention, in general the shelf life of a product is the period, starting from its manufacture, during which the product remains suitable for consumption. In particular, during its shelf-life, the product maintains an acceptable microbiological quality, maintains fluidity, a pH in the range of 3 to 5, 9 to 20 g per 100 ml of non-hydrolysed globular protein, fat and at least 100 mg of divalent metal cations in the product per 100 ml of said product. In a preferred embodiment, the product maintains a viscosity of about 200 mPa·s or less, more preferably of 100 mPa·s or less during its shelf life.

The term "about" is in particular used herein to indicate a range of ±10%, more in particular of ±5% around a given value.

Globular Proteins

The invention is generally concerned with globular proteins. Globular proteins may be single peptide chains, two peptide chains or more peptide chains which interact in the usual ways. A globular protein may have portions of the chains with helical structures, pleated structures, or completely random structures. Globular proteins are relatively spherical in shape as the name implies. In the art, globular proteins are described as proteins of which the protein chain, including the secondary structure elements, is tightly folded into a more or less spherical shape (cf. Dairy Science and Technology, 2$^{nd}$ ed. ISBN 0-8247-2763-0). The tertiary structure assumed by a globular protein molecule tends to be such that the non-polar side chains are directed inward to allow interaction with one another and the polar side chains are typically oriented outward such that they are exposed to adjacent polar water molecules. A globular protein herein is to be understood as a protein which is globular in its non-denatured state. They are distributed in both plant and animal tissues. For instance, albumins can be found in blood (serum albumin), milk (lactalbumin), egg white (ovalbumin), lentils (legumelin), kidney beans (phaseolin), and wheat (leucosin). Globulins can be found in blood (serum globulins), muscle (myosin), potato (tuberin), Brazil nuts (excelsin), hemp (edestin), whey (lactoglobulins, immunoglobulins, and lactoferrins), pea and lentils (legumin, vicilin), and soy. Also, many enzymes and other vegetable proteins are globular proteins. More specifically, the invention is concerned with globular protein selected from the group consisting of whey protein, pea protein, soy protein, and any mixture thereof, more in particular with whey proteins.

When referred herein to a "non-hydrolysed" globular protein, this means that the protein is fully intact or only to a minor extent contains hydrolysed fragments. A minor extent is an extent in which the globular nature of the protein is essentially maintained. The hydrolysed fragments—if present at all—in particular make up less than 10 weight %, such as, for instance 1 to 5 weight % relative to the total weight of the globular protein.

Hence, with the term globular protein is meant the collection of proteins which are globular in nature, but may contain minute amounts of hydrolysed fragments and/or uncoiled fragments.

The amount of non-hydrolysed globular protein, preferably whey, ranges between 9 and 20 g per 100 ml. Preferably, the amount of non-hydrolysed globular protein, preferably whey, ranges between 9 and 16 g per 100 ml. Advantageously, the lower limit in the amount of non-hydrolysed globular protein, preferably whey, is any of 9, 10, 11, 12, 13, 14, 15, 16, 17, 18 or 19 g per 100 ml. Advantageously, the upper limit in the amount of non-hydrolysed globular protein, preferably whey, is any of 20, 19, 18, 17, 16, 15, 14, 13, 12, 11 or 10 g per 100 ml. More preferably, the amount of non-hydrolysed globular protein, preferably whey, ranges between 9 and 20, or 9 and 18, or 9 and 16, or 9 and 14, or 9 and 12, or 10 and 20, or 10 and 18, or 10 and 16, or 10 and 15, or 10 and 14, or 10 and 12 g per 100 ml. In a specific embodiment, the amount of non-hydrolysed globular protein, preferably whey, is equal to about 10 g per 100 ml of the composition. Preferably, the amount of non-hydrolysed globular protein is at least 85 weight % of the total proteinaceous matter in the composition according to the invention, the rest of the proteinaceous matter being selected from the group comprising a non-globular protein, a hydrolysed protein, an oligopeptide, a peptide and a free amino acid.

In a specific embodiment, the non-globular protein is selected from the group of casein, caseinate, micellar casein isolate, and any mixture thereof.

In a specific embodiment, the free amino acid is selected from the group of branched chain amino acids and salts thereof; in a particular embodiment, the free amino acid is L-leucine.

Whey Proteins

One of the most superior classes of food protein is whey protein. It has an excellent amino acid profile for a purpose of the invention, high amount of cystein, rapid digestion, and interesting bioactive proteins (lactoglobulins, immunoglobulins, and lactoferrins). Nutritionally speaking, whey protein is known as a naturally complete protein because it contains all of the essential amino acids required in the daily diet. It is also one of the richest sources of branched chain amino acids (BCAAs, in particular leucine) which play an important role in muscle protein synthesis. Moreover, some of the individual components of whey protein have been shown to prevent viral and bacterial infection and modulate immunity in animals. Whey protein is the preferred choice of proteins to treat persons suffering from sarcopenia, but is also suitable for healthy persons, such as sportsmen and (active) elderly.

As a source of whey protein to be used in the present invention, any commercially available whey protein source may be used or any. whey obtained by any process for the preparation of whey known in the art, as well as whey protein fractions prepared thereof, or the proteins that constitute the bulk of the whey proteins being β-lactoglobulin, α-lactalbumin and serum albumin, such as liquid whey, or whey in powder form, such as whey protein isolate (WPI) or whey protein concentrate (WPC). Whey protein concentrate is rich in whey proteins, but also contains other components such as fat and lactose. Furthermore, whey originating from sweet whey may contain glycomacroprotein (GMP), a caseine-related non-globular protein, which is also soluble at a pH at which the whey proteins are soluble and hence, difficult to separate therefrom. Typically, whey protein concentrate is produced by membrane filtration. On the other hand, whey protein isolate consists primarily of whey proteins with minimal amounts of fat and lactose. Whey protein isolate usually requires a more rigorous separation process such as a combination of microfiltration and ultra-filtration or ion exchange chromatography. It is generally understood that a whey protein isolate refers to a mixture in which at least 90 weight % of the solids are whey proteins. A whey protein concentrate is understood as having a percentage of whey proteins between the initial amount in the by-product (about 12 weight %) and a whey protein isolate. In particular, sweet whey, obtained as a by-product in the manufacturing of cheese, acid whey, obtained as a by-product in the manufacturing of acid casein, native whey, obtained by milk microfiltration or rennet whey, obtained as a by-product in the manufacturing of rennet casein, may be used alone or in combination as source of globular whey proteins.

Furthermore, whey proteins may originate from all kinds of mammalian animal species, such as, for instance cows, sheep, goats, horses, buffalo's, and camels. Preferably, the whey protein is of bovine origin.

Preferably, the whey protein source, used for preparing a product according to the invention, is available as a powder, preferably the whey protein source is selected from the group consisting of whey protein concentrate (WPC), whey protein isolate (WPI), and any mixture thereof.

According to a specific embodiment, the whey is a mixture of non-acidified (i.e. neutral) WPI and acidified WPI. Amounts of acidified and non-acidified WPI may range between 10 weight % and 90 weight %, such that any weight ratio is obtained between 10/90 and 90/10. Preferably, the weight ratio acidified:neutral whey is in the range of 50:50 to 70:30. A weight ratio acidified:neutral whey of about 60:40 is particularly preferred.

Whey protein isolate consists mainly of a mixture of β-lactoglobulin, α-lactalbumin and serum albumin, and optionally GMP if the whey source is sweet whey. The three first proteins are globular proteins that are sensitive to aggregation in the denaturated state. The denaturation temperature of β-lactoglobulin is pH-dependent; at pH 6.7, irreversible denaturation occurs when the protein is heated at temperatures above about 65° C. In the denaturated state, a free thiol group is exposed. This free thiol group can initiate inter-protein disulfide interactions leading to a polymerization reaction resulting in aggregate formation. Also two disulfide bridges, present in native β-lactoglobuline, are involved in the polymerization reaction and also other sulphur containing groups including cysteine residues are thought to play a role.

α-Lactalbumin also has a denaturation temperature of about 65° C. Since α-lactalbumin does not have a free thiol group (only four disulfide bridges), solutions of pure α-lactalbumin are not irreversibly denaturated under most processing conditions. However, in the presence of β-lactoglobulin, as is the case in e.g. a whey protein concentrate or isolate, α-lactalbumin is more sensitive to irreversible denaturation through the formation of α-lactalbumin/β-lactoglobulin complexes in which also disulfide bridges in β-lactoglobuline and α-lactalbumin are involved via interchange reactions. Also, the circumstance that α-lactalbumin contains cystein residues is considered to contribute to a certain sensitivity to irreversible denaturation.

Denaturated β-lactoglobulin and α-lactalbumin are both sensitive to calcium; this is particularly the case in the pH range of about 5 to about 8 where the protein carries a neutral to net negative charge. At pH 4, the protein carries a net positive charge and is less (but still) sensitive to calcium-induced aggregation.

The size, shape and density of the protein aggregates in a matrix are influenced by a number of environmental and processing parameters including temperature, heating rate, pressure, shear, pH and ionic strength and other ingredients in the matrix, such as, for instance carbohydrates, minerals, acids, fat, etc. Depending on the combination of these parameters and ingredients, the aggregates may form a space-filling network (gel), fibrils or compact micro-particles. For example, microparticulated whey can be formed under specific ionic strength and shear conditions. These particles have a compact structure, a high intrinsic viscosity and a low specific volume. Further, it is known that a relationship exists between aggregates size and heating temperature for microparticulated whey produced under shear conditions. Microparticulated whey protein has received a lot of interest lately for application as a fat replacer or viscosity enhancer for yoghurt.

One of the major problems encountered with the production of liquid ready-to-use compositions containing globular proteins in general, and whey proteins in particular, is their limited processability and heat-sensitivity. As these proteins are heated above their denaturation temperature in a sterilization process, they unfold and are transformed into a reactive state, polymerize into aggregates or gels. As a consequence, the heat-treated liquid composition exhibits unwanted sensorial attributes like chalkiness, sandiness, lumpiness. Besides, the shelf life of these products is limited in that sediment and/or cream layers are formed soon after production or in that age-thickening occurs. In a composition with a high amount of globular protein, in particular whey, these instabilities are even more pronounced and result in products with an unwanted high viscosity and extensive fouling and blocking of the heating equipment.

Surprisingly, the inventors have now found that it is possible to prepare a sterilized liquid or semi-solid acid enteral nutritional composition by means of a method wherein a composition that comprises mainly globular proteins as a protein source, in particular whey proteins, is subjected to a specific heat-treatment that comprises a step of subjecting the whey proteins to a DSI treatment at conditions which may be insufficient per se to sterilize or pasteurize the composition comprising the globular proteins, in particular whey proteins.

Without being bound (or restricted) by theory, it is believed that raising the temperature has a different effect on both denaturation and aggregation. While under a temperature of about 100° C., the rate of aggregation is higher than the rate of denaturation, this behaviour is quickly reversed at temperature above about 100° C. At a temperature below about 100° C., heating leads to the formation of long protein strains that may form disulfide bonds and aggregate and form large particles that eventually sedimentate. At a temperature above about 100° C., globular proteins quickly start to denaturate. Hence, a slow heat-treatment just above the denaturation temperature of the whey leads to extensive polymerization and voluminous protein aggregates. Also, when the whey is heated to high temperatures (i.e. far above the protein denaturation temperature, for example at about 110° C.) via a slow heating process, i.e. a process in which the temperature of the protein solution is raised gradually, for example 0.1 to 2° C. per second, using e.g. retort, plate or tubular heat exchangers, the whey exhibits extensive polymerization during heating up when process temperatures pass the temperature window just above the denaturation temperature of the whey protein. As a result, the product is too thick, lumpy, sandy and extensive fouling is observed in the heating apparatus, in particular when high amounts of calcium are present per 100 ml of composition, such as, for instance more than 100 mg, more in particular more than 200 mg in compositions comprising 9 to 20 gram of globular protein, in particular whey protein.

Using the method according to the invention, by quickly and shortly heating the globular proteins well above the denaturation temperature of the whey protein, the thiol group of β-lactoglobulin, the main constituent of whey protein, is very quickly being exposed and termination reactions forming disulfide bridges dominate initially after heating. As a result, small, compact whey protein particles are formed which are largely inert in any further heat-treatment. Hence, surprisingly, it was found that the time for whey proteins to be spent in a temperature window just above the denaturation temperature, should be minimized.

Surprisingly, as a result of said treatment, a resulting sterilized liquid or semi-solid acid enteral nutritional composition has a long shelf life, typically at least 6 months, preferably 12 months or more, satisfactory organoleptic properties, such as no or a low astringency and/or no or a low sandiness compared to a prior art sterilized liquid or semi-solid acid enteral nutritional composition.

Stabilizing Polysaccharide

In a preferred embodiment of this invention, the sterilized liquid or semi-solid acid enteral nutritional composition also comprises a polysaccharide capable of stabilizing the small compact protein particles that are formed in the heat-treatment. These polysaccharides are also referred to herein as "stabilizing polysaccharides".

Without limiting the scope of the invention, it is hypothesized that certain polysaccharides having both positively and negatively charged groups or regions at a pH below the isoelectric point (IEP) of whey protein. At such a pH the protein will have a net positive charge, which is assumed to interact with the negatively charged groups of the polysaccharide. This interaction results in the protein particle being surrounded by the large polysaccharide molecules decreasing the likelihood of protein particles coming within close distance of each other and aggregate. Furthermore, it is hypothesized that the long polysaccharide chains can form networks within the liquid matrix preventing sedimentation of the protein particles.

Hence, in a preferred embodiment the stabilizing polysaccharide is a polysaccharide having positively as well as negatively charged groups at a pH within the range of 3-5, e.g. at a pH of 4.2. Furthermore, it is preferred that the stabilizing polysaccharide does not interact with the calcium ions to form firm gel structures. Polysaccharides that may suitably be used for the purposes of the present invention include high methoxy pectin and carboxymethyl cellulose. Preferred examples of carboxymethyl celluloses that may suitably be used in accordance with the invention, include Clear+Stable 30 PA, Clear+Stable 100 PA and Clear+Stable 2000 PA (Dow chemical). The term "high methoxy pectin" herein is to be understood as a methoxy pectin wherein at least 50% of the galacturonic acid groups are esterified with a methyl group.

In one embodiment of the invention, the stabilizing polysaccharide is high methoxy pectin, which is typically used in a concentration of 0.01-1% (w/v), preferably 0.02-0.5% (w/v), more preferably 0.05-2% (w/v), for example in a concentration of 0.1% (w/v).

In another embodiment of the invention, the stabilizing polysaccharide is carboxy methyl cellulose, which is typically used in a concentration of 0.1-10% (w/v), preferably 0.2-5% (w/v), more preferably 0.5-3% (w/v), most preferably in a concentration of 1-2% (w/v).

Direct Steam Injection

Direct Steam Injection (DSI) involves the discharge of steam (water at a temperature above 100° C.) into a liquid with a lower temperature than the steam. The steam condenses and gives up its heat to the surrounding liquid. As heat is transferred by direct contact between the steam and the liquid, consequently this method is only used when dilution and an increase in liquid mass is acceptable. Therefore, the liquid being heated is usually water or an aqueous composition, such as a nutritional composition. Furthermore, after flash-cooling of the heated liquid, most of the added steam is lost again by evaporation under vacuum. DSI is used in the food industry since the early 1930s for use as a sterilization treatment, and its principles are known to the skilled person and will not be further disclosed herein in detail. Commercial apparatus can be bought e.g. from the company Tetra Pak Processing Systems BV, Houten, The Nether-lands.

In this application, DSI is applied for non-sterilizing purposes, mostly at non-sterilizing conditions. An overview of the DSI conditions according to this application, in comparison with the conditions for UHT treatment is shown in FIG. 1.

Recently, the use of DSI for non-sterilizing purposes has been disclosed in WO2007/108827 (Abbott) for the reduction of the viscosity of a high energy (225-325 kcal/ml) milk protein isolate composition (comprising about 20% of whey) for MPI amounts of between 6.7 and 12.6 g/100 ml (which corresponds to about 1.3 to 2.5 g whey per 100 ml of liquid composition. However, no examples were given, illustrating the claimed effect, nor is disclosed that the effect is related to a reduction of astringency or that is can be applied to predominantly whey-based compositions, such as comprising 9 to 20 g/100 ml of whey proteins.

Method of Preparation of the Composition

The invention provides a method for the preparation of a sterilized liquid or semi-solid acid enteral composition comprising 9 to 20 g of non-hydrolysed globular proteins, fat and at least 100 mg of divalent metal cations and having a pH ranging between 3 and 5, comprising a step wherein at least the non-hydrolysed globular proteins are subjected to a direct steam injection (DSI) at specific holding values, such as a holding temperature of 100 to 140° C. during a holding time of about 0.5 to 10 seconds, preceded by a homogenization step.

In a preferred embodiment of the invention, a process as defined above is provided wherein the step wherein at least the non-hydrolysed globular protein is subjected to DSI treatment, is followed by a sterilization step.

As will be understood by those skilled in the art, the DSI treatment as described herein may result in the liquid or semi-solid becoming sterilized or 'commercially sterile' without performing a separate sterilization, depending on e.g. the conditions applied during the DSI treatment. Hence, embodiments wherein the process described above is not followed by a separate sterilization step are also within the scope of this invention.

In another preferred embodiment of the invention, a process as defined above is provided wherein at least the non-hydrolysed globular protein and a stabilizing polysaccharide are subjected to homogenization followed by DSI treatment and, optionally, a sterilization step.

The invention also provides a method for the preparation of a sterilized liquid or semi-solid acid enteral nutritional composition comprising per 100 ml of said composition 9 to 20 g of non-hydrolysed globular protein, fat, and at least 100 mg of divalent metal cations and having a pH ranging between 3 and 5, comprising the consecutive steps of:

a) preparing an aqueous solution comprising amounts of divalent metal cations, in particular calcium and magnesium, non-hydrolysed globular proteins, fat, and, optionally, the stabilizing polysaccharides, such that said sterilized liquid or semi-solid acid enteral composition comprises per 100 ml of said composition 9 to 20 g of non-hydrolysed globular proteins, fat, at least 100 mg of divalent metal cations and, optionally the stabilizing polysaccharide, and having a pH ranging between 3 and 5;

b) homogenizing the resulting solution essentially obtained by step a);

c) subjecting the resulting solution essentially obtained by step b) to a direct steam injection process at a holding temperature of 100 to 140° C. during a holding time of about 0.5 to 10 seconds; and, optionally, d) subjecting the resulting solution essentially obtained by step c) to a sterilization treatment.

With "consecutive" is meant that the order in which the steps are implemented is: step a) followed by step b), followed by step c), followed by (optional) step d). Steps implementing other actions may be intermittently added to the sequence of steps a), b), c) and d), with the proviso the order of the steps a), b), c) and (optionally) d) is not changed. Typical steps that may be added are:

preparing other solutions;
dissolving other macro constituents of a nutritional composition (e.g. carbohydrates, fibres);
dissolving other constituents such as minerals, amino acids, etc.;
mixing;
preheating;
adjusting the pH;
flash-cooling.

In a particularly preferred embodiment of this invention, a method for the preparation of a sterilized semi-solid acid enteral composition, also referred to as 'spoonable composition', is provided as described in any of the foregoing, comprising the additional step f) of adding a thickener or gelling agent to the liquid prior to or after DSI treatment.

With "the resulting solution essentially obtained" is meant the solution essentially resulting from a previous process step, with the proviso that the solution may contain other components as a consequence of an intermitting process step e), such as, but not limited to, the addition of other nutritional components.

A preferred process according to the present invention for the preparation of a sterilized liquid or semi-solid acid enteral composition according to the invention, comprises the consecutive steps of:

e1) dissolving an amount of non-hydrolysed globular proteins in a first aqueous solution, such that said sterilized liquid or semi-solid acid enteral composition obtained comprises per 100 ml of said composition 9 to 20 g of non-hydrolysed globular proteins;

e2) dissolving an amount of minerals comprising divalent metal cations, in particular calcium and magnesium, in a second aqueous solution, such that said sterilized liquid or semi-solid acid enteral composition obtained comprises per 100 ml of said composition at least 100 mg of divalent metal cations; preferably, this is performed at a pH of about 4.3.

e3) mixing the second aqueous solution comprising divalent metal cations, in particular calcium and magnesium, with the first aqueous solution comprising an amount of non-hydrolysed globular proteins such that said sterilized liquid or semi-solid acid enteral composition obtained comprises per 100 ml of said composition 9 to 20 g of non-hydrolysed globular proteins and at least 100 mg of divalent metal cations;

e4) adding an amount of fat, preferably a liquid fat, to the resulting solution essentially obtained from step e3)

b) homogenizing the resulting solution essentially obtained by step e4);

e5) preheating the resulting solution essentially obtained by step b);

c) subjecting the resulting solution essentially obtained by step e5) to a direct steam injection process at a holding temperature of 100 to 140° C. during a holding time of about 0.5 to 10 seconds;

e6) flash-cooling the resulting solution essentially obtained by step c);

e7) optionally, adjusting the pH of the resulting solution obtained by step e6); and, optionally, d) subjecting the resulting solution essentially obtained by step e7) to a sterilization treatment.

A preferred process according to the present invention for the preparation of a sterilized liquid or semi-solid acid enteral composition comprising per 100 ml of said composition 9 to 20 g of non-hydrolysed globular proteins, fat, and carbohydrates according to the invention, comprises the consecutive steps of:

e1) dissolving an amount of non-hydrolysed globular proteins and an amount of carbohydrates in a first aqueous solution, such that said sterilized liquid or semi-solid acid enteral composition obtained comprises per 100 ml of said composition 9 to 20 g of non-hydrolysed globular proteins;

e2) dissolving an amount of minerals comprising divalent metal cations, in particular calcium and magnesium, in a second aqueous solution, such that said sterilized liquid or semi-solid acid enteral composition obtained comprises per 100 ml of said composition at least 100 mg of divalent metal cations; preferably, this is performed at a pH of about 4.3.

e3) mixing the second aqueous solution comprising divalent metal cations, in particular calcium and magnesium, with the first aqueous solution comprising an amount of non-hydrolysed globular proteins and an amount of carbohydrates such that said sterilized liquid or semi-solid acid enteral composition obtained comprises per 100 ml of said composition 9 to 20 g of non-hydrolysed globular proteins and at least 100 mg of divalent metal cations;

e4) adding an amount of fat, preferably a liquid fat, to the resulting solution essentially obtained by step a);

b) homogenizing the resulting solution essentially obtained by step e4);

e5) preheating the resulting solution essentially obtained by step b);

c) subjecting the resulting solution essentially obtained by step e5) to a direct steam injection process at a holding temperature of 100 to 140° C. during a holding time of about 0.5 to 10 seconds;

e6) flash-cooling the resulting solution essentially obtained by step c);

e7) optionally, adjusting the pH of the resulting solution obtained by step e6); and, optionally, d) subjecting the resulting solution essentially obtained by step e7) to a sterilization treatment.

Another preferred process according to the present invention for the preparation of a sterilized liquid or semi-solid acid enteral composition according to the invention, comprises the consecutive steps of:

e1) dissolving an amount of non-hydrolysed globular proteins and a stabilizing polysaccharide in a first aqueous solution, such that said sterilized liquid or semi-solid acid enteral composition obtained comprises per 100 ml of said composition 9 to 20 g of non-hydrolysed globular proteins;

e2) dissolving an amount of minerals comprising divalent metal cations, in particular calcium and magnesium, in a second aqueous solution, such that said sterilized liquid or semi-solid acid enteral composition obtained comprises per 100 ml of said composition at least 100 mg of divalent metal cations; preferably, this is performed at a pH of about 4.3.

e3) mixing the second aqueous solution comprising divalent metal cations, in particular calcium and magnesium, with the first aqueous solution comprising an amount of non-hydrolysed globular proteins such that said sterilized liquid or semi-solid acid enteral composition obtained comprises per 100 ml of said composition 9 to 20 g of non-hydrolysed globular proteins and at least 100 mg of divalent metal cations;

e4) adding an amount of fat, preferably a liquid fat, to the resulting solution essentially obtained from step e3);

b) homogenizing the resulting solution essentially obtained by step e4);

e5) preheating the resulting solution essentially obtained by step b);

c) subjecting the resulting solution essentially obtained by step e5) to a direct steam injection process at a holding temperature of 100 to 140° C. during a holding time of about 0.5 to 10 seconds;

e6) flash-cooling the resulting solution essentially obtained by step c); and, optionally, e7) adjusting the pH of the resulting solution obtained by step e6).

Step e1) is preferably performed at 1 to 70° C., preferably at 20 to 55° C. At higher temperatures, less foaming is observed. The proteins are dissolved in a volume of an aqueous solution, preferably water such as, for instance demineralised water, demi-water or tap water, such that, after dilution with other solutions in subsequent steps, an end volume is obtained such that this end volume comprises 9 to 20 g of non-hydrolysed globular proteins per 100 ml of sterilized liquid or semi-solid acid enteral composition.

Step e2) is preferably performed at 1 to 90° C., preferably at 20 to 30° C. Preferably, this step is performed at a pH of about 4.3. At this pH, minerals (in the form of salts, hydroxides, etc.) dissolve most easily. The minerals are dissolved in a volume of an aqueous solution, preferably water such as, for instance demineralised water, demi-water or tap water, such that, after dilution with other solutions in subsequent steps, an end volume is obtained such that this end volume comprises at least 100 mg of non-hydrolysed globular proteins per 100 ml of sterilized liquid or semi-solid acid enteral composition.

Preferred embodiments of the invention provide any of the above defined processes, wherein the step e7) of adjusting the pH of the solution obtained by step e6) is performed. Furthermore, in an embodiment it is preferred that steps e7) and d) are both performed.

Step a) is preferably performed at 1 to 90° C., preferably at 20 to 30° C.

Step b) is preferably performed at 1 to 90° C., preferably at 60 to 70° C. Preferably, the mixture is pumped by a high pressure pump through a narrow opening, a valve. Due to the very narrow opening a high speed is introduced. When the pressure is 60 MPa (600 Bar.) the maximal velocity will be about 600 m/s. The potential energy will be transformed in kinetic energy resulting in an increase in temperature and heavy turbulence. The increase in temperature corresponds with P/4, so homogenisation at 60 MPa results in a temperature rise of 15° C. The heavy turbulence results in a disruption of the fat globules. Since the residence time of the product in the valve is so short, an enormous energy density is created ($10^{11}$-$10^{12}$ $Wm^{-3}$). As a consequence of the high energy density, the oil droplets are disrupted into smaller droplets. Since the energy dissipation is not constant, the droplets formed will vary in size, so a particle size distribution will be created. The better the valve of the homogeniser, the smaller the particle size distribution. If a valve is not in perfect state, a wider particle size distribution will be produced giving bigger droplets which can create product problems such as creaming.

Other steps may be performed at such temperatures that can easily be selected by the skilled person, without any inventive activity, depending on e.g. the apparatus used.

Divalent Metal Cations

With the term "divalent metal cation" is meant any positive charged metal ion with a charge equal to two. In particular is meant the ions of magnesium ($Mg^{2+}$), calcium ($Ca^{2+}$), zinc ($Zn^{2+}$) and iron ($Fe^{2+}$), preferably calcium ($Ca^{2+}$) as these ions appear at relative high concentrations in nutritional compositions, in particular to comply with FSMP regulations. Preferably, the composition according the invention is a nutritionally complete composition.

In an embodiment of the present invention, the amount of divalent metal ions is at least 100 mg of divalent metal cations per 100 ml of composition.

Preferably, the amount of divalent metal ions ranges between 100 mg/100 ml and 600 mg/100 ml and preferably between 200 mg/100 ml and 500 mg/100 ml. In a specific embodiment, the amount of divalent cations is about 270 mg/100 ml.

Preferably, the divalent metal cation is selected from the group consisting of Ca, Mg and any mixture thereof, preferably Ca.

Preferably, the amount of calcium ranges between 100 mg/100 ml and 600 mg/100 ml and more preferably between 200 mg/100 ml and 500 mg/100 ml. In a further embodiment, the amount of calcium is about 250 mg/100 ml.

Preferably, the amount of magnesium ranges between 10 mg/100 ml and 100 mg/100 ml and more preferably between 15 mg/100 ml and 70 mg/100 ml. In a further embodiment, the amount of magnesium is about 19 mg/100 ml.

Fat

According to the invention, the present sterilized liquid or semi-solid acid enteral composition should comprise an amount of fat (i.e. lipid). The amount of fat may range between 5 and 95%, preferably between 10 and 70%, more preferably between 15 and 65%, relative to the total energy amount of the composition.

With regard to the type of fat, a wide choice is possible, as long as the fat is of food quality. In an advantageous embodiment, the composition comprises a fat which is liquid under ambient conditions, i.e. at room temperature and a pressure of 1 atm.

The fat may either be an animal fat or a vegetable fat or both. Although animal fats such as lard or butter have essentially equal caloric and nutritional values and can be used interchangeably, vegetable oils are highly preferred in the practice of the present invention due to their readily availability, liquid form, ease of formulation, absence of cholesterol and lower concentration of saturated fatty acids. In a further embodiment, the present composition comprises rapeseed oil, corn oil and/or sunflower oil.

The fat may include a source of medium chain fatty acids, such as medium chain triglycerides (MCT, mainly 8 to 10 carbon atoms long), a source of long chain fatty acids, such as long chain triglycerides (LCT, mainly at least 18 carbon atoms long) and phospholipid-bound fatty acids such as phospholipid-bound EPA or DHA, or any combination of the two types of sources. MCTs are beneficial because they are easily absorbed and metabolized in a metabolically-stressed patient. Moreover, the use of MCTs will reduce the risk of nutrient malabsorption. LCT sources, such as canola oil, rapeseed oil, sunflower oil, soybean oil, olive oil, coconut oil, palm oil, linseed oil, marine oil or corn oil are beneficial because it is known that LCTs may modulate the immune response in the human body.

In a specific embodiment, the fat comprises 30 to 60 weight % of animal, algal or fungal fat, 40 to 70 weight % of vegetable fat and optionally 0 to 20 weight % of MCTs based on total fat of the composition. The animal fat preferably comprises a low amount of milk fat, i.e. lower than 6 weight %, especially lower than 3 weight % based on total fat. In particular, a mixture of corn oil, egg oil, and/or canola oil and specific amounts of marine oil is used. Egg oils, fish oils and algal oils are a preferred source of non-vegetable fats. Especially for compositions that are to be consumed orally, in order to prevent formation of off-flavours and to decrease a fishy after-taste, it is recommended to select ingredients that are relatively low in docosahexaenoic acid (DHA), i.e. less than 6 weight %, preferably less than 4 weight % based on total fat. Marine oils containing DHA are preferably present in the composition according to the invention in an amount lower than 25 weight %, preferably lower than 15 weight % based on total fat. On the other hand, inclusion of eicosapentaenoic acid (EPA) is highly desirable for obtaining the maximum health effect. Therefore, in another embodiment, the amount of EPA may range between 4 weight % and 15 weight %, more preferably between 8 weight % and 13 weight % based on total fat. The weight ratio EPA:DHA is advantageously at least 6:4, for example between 2:1 and 10:1. In yet another embodiment, the amount of EPA is very low, such as 0.1 to 1 weight %, preferably 0.3 weight % or 0.6 weight %, based on total fat.

Also, the sterilized liquid or semi-solid acid enteral composition according to the invention may beneficially comprise an emulsifier. In principle, any food-grade emulsifier may be present. Suitable emulsifiers are commonly known. Generally the emulsifier contributes to the energy amount of the fat in said composition.

Digestible Carbohydrate

In a specific embodiment of the present invention, the sterilized liquid or semi-solid acid enteral composition according to the invention further comprises a digestible carbohydrate. Preferably, the digestible carbohydrate provides between 20 to 60% of the total energy amount of the composition according to the invention. The digestible carbohydrate may comprise either simple or complex carbohydrates, or any mixture thereof. Suitable for use in the present invention are glucose, fructose, sucrose, lactose, trehalose, palatinose, corn syrup, malt, maltose, isomaltose, partially hydrolysed corn starch, maltodextrins, glucose oligo- and poly-saccharides.

The composition of the digestible carbohydrate preferably is such that high viscosities, excessive sweetness, excessive browning (Maillard reactions) and excessive osmolarities are avoided. Acceptable viscosities and osmolarities may be achieved by adjusting the average chain length (average degree of polymerisation, DP) of the digestible carbohydrates between 1.5 and 6, preferably between 1.8 and 4. In order to avoid excessive sweetness, the total level of sucrose and fructose is preferably less than 60%, more preferably less than 52%, more preferably less than 40% of the weight of the carbohydrate, especially of the digestible carbohydrate. Long-chain digestible carbohydrates such as starch, starch fractions and mild starch hydrolysates (DE≥6, DE<20), may also be present, preferably in an amount of less than 25 weight %, especially less than 15 weight % of the digestible carbohydrate, and less than 6 g/100 ml, preferably less than 4 g/100 ml of the total liquid enteral composition according to the invention.

Vitamins, Minerals and Trace Elements

The sterilized liquid or semi-solid acid enteral composition according to the invention may also contain a variety of vitamins, minerals and trace elements.

In one embodiment of the present invention, the sterilized liquid or semi-solid acid enteral composition according to the invention provides all necessary vitamins, most of the minerals and trace elements. For example, the composition according to the invention preferably provides about 1.1 mg of zinc per 100 ml of the composition which is beneficial for tissue repair in a healing patient. Preferably, the composition according to the invention provides 16 mg of vitamin C per 100 ml of the composition to aid patients with more severe healing requirements. Further, preferably, the composition according to the invention provides 1.2 mg iron per 100 ml of the composition. Iron is beneficial in maintaining bodily fluids as well as circulatory system functions in an elderly patient.

The phosphorus amount may be above 10 mg per g of protein, and may amount to, for instance, 125 mg/100 ml of total composition with a calcium to phosphorus weight ratio between about 1 and about 3. In a further embodiment, the ratio is about 2.

Other ingredients may be present, such as vitamin A, carotenoids, vitamin D3, vitamin E, vitamin K, thiamin, riboflavin, niacin, panthotenic acid, vitamin B6, folic acid, vitamin B12, biotin, vitamin C, choline, lecithine and trace elements such as copper, manganese, selenium, molybdenum, chromium en iodine.

Thickener/Gelling Agent

As stated before, in an embodiment of the present invention, a liquid composition according to the invention may be used as the basis for the manufacturing of a semi-solid nutritional composition, also referred to as 'spoonable composition', such as a créme, a pudding, a custard, a soup, an ice cream, or a jelly. To this end, a liquid composition according to the invention is processed to convert the low viscosity composition according to the invention into a more solid or viscous one, e.g. by adding thickeners or gelling agents and further process the mixture into the final semi-solid product, e.g. by subjecting it to a heat-treatment. Thickeners and/or gelling agents can also be present in the formulation from an earlier stage of the process, or even dissolved together with the nutrients at the beginning of the process. Hence, according to one embodiment, the invention is related to a semi-solid enteral nutritional composition obtainable from a nutritional composition comprising per 100 ml of said composition 9 to 20 g of non-hydrolysed globular protein, fat, and at least 100 mg of divalent metal cations and having a pH ranging between 3 and 5, by combining with a thickener or gelling agent.

Many conventional thickeners and/or gelling agents can be used in accordance with the invention, including various gums, such as locust bean gum, guar gum, xanthan gum, gum arabic, carob gum, etc.; alginates; agar; carrageenan; cellulose and cellulose derivatives; starches, including modified starches, pectins, etc. In a preferred embodiment of the invention starch or pectin is used as thickener or gelling agent.

In one embodiment of the invention, the thickener or gelling agent is pectin, which is typically used in a concentration of 0.05-5% (w/v), preferably 0.1-1% (w/v), more preferably 0.2-0.5% (w/v), for example in a concentration of 0.35% (w/v).

In another embodiment of the invention, the thickener or gelling agent is starch, which is typically used in a concentration of 0.1-10% (w/v), preferably 0.2-5% (w/v), more preferably 0.5-2% (w/v), for example in a concentration of 1% (w/v). In another embodiment the thickener is applied in amounts sufficient to give the product the desired viscosity and/or structure. Preferably the viscosity of a semi-solid product, also referred to herein as a spoonable product, is within the range between 200-2500 mPa·s, preferably 300-2000 mPa·s, more preferably 400-1000 mPa·s, all measured at 20° C. at a shear rate of 100 s$^{-1}$. Such products, meaning also spoonable products, are products that can readily be consumed by spooning up the product from a container or plate.

In accordance with the present invention, liquid products are typically products that are pourable (at 20° C.), in particular pourable from an opened container in which they are contained. In particular, a product is liquid or pourable if its viscosity, as measured using the method as described in the definitions section, lies below 200 mPa·s.

In another preferred embodiment of the invention the spoonable product has the form of a hydrogel.

In one embodiment of the invention the composition comprises a polysaccharide that functions as a thickener as well as a stabilizer. For example, high methoxy pectin may be used in amounts sufficient to convert the product into a more viscous or more solid product, which at the same time will aid in the stabilization of the protein particles typically through the mechanisms explained herein before. In a particularly preferred embodiment the semi-solid composition comprises a combination of high methoxy pectin and a starch, typically in amounts sufficient to impart the desired viscosity and to confer the stabilizing action described herein before.

Nutritional Compositions

According to a preferred embodiment, the liquid enteral nutritional composition according to comprises:
a) about 10 g of non-hydrolysed whey per 100 ml of the composition, said protein providing about 56% of the total energy amount of the composition;
b) fat providing about 18% of the total energy amount of the composition;
c) optionally carbohydrate providing about 23% of the total energy amount of the composition,
d) about 250 mg per 100 ml of Ca and about 19 mg per 100 ml of Mg; and
e) having a pH of about 4.

Medical Use

The nutritional composition according to the invention can advantageously be used for the nutritional management of a person in need thereof, in particular wherein the person is an elderly person, a person that is in a disease state, a person that is recovering from a disease state, a person that is malnourished, a sportsman, or an active elderly. The nutritional composition according to the invention can advantageously be used for the prevention or treatment of a disease or condition involving muscle decline in a mammal. Alternatively, the nutritional composition according to invention can advantageously be used for the prevention or treatment of a disease or condition selected from the group of sarcopenia, muscle loss, insufficient muscle protein synthesis, muscle degradation, muscle proteolysis, muscle atrophy, muscle dystrophy, muscle catabolism, muscle wasting, loss of muscle strength, loss of muscle mass, loss of muscle function, loss of physical capacity, loss of physical performance, impaired mobility, frailty, surgery, disability, risk of falling and risk of fall-related fractures in a mammal. Preferably, said adult mammal is an elderly human.

The term "nutritional management" herein is to be understood as the provision to a person of an amount of a nutrient or nutrients which corresponds to the recommended daily nutritional intake of that nutrient or those nutrients for that person, in particular an elderly person. In order to determine for an individual what the recommended amount of the liquid or semi-solid acid enteral nutritional composition according to the invention to be taken should be to nutritionally manage this person in a desired manner, the skilled person has several detailed sources of information at his disposal to achieve this. For instance, specific tables or other sources of information from governmental authorities, such as the Food and Nutrition Information Center of the United States Department of Agriculture, can be consulted to allow a person to be provided with an amount of a nutrient or nutrients which corresponds to the recommended daily nutritional intake of that nutrient or those nutrients for that person, in particular an elderly person.

Dosage

In a specific embodiment, the nutritional composition according to the invention has the form of a complete food, i.e. it can meet all nutritional needs of the user. As such, it preferably contains 1200 to 2500 kcal per daily dosage. The daily dosage amounts are given with respect to a daily energy supply of 2000 kcal to a healthy adult having a body weight of 70 kg. For persons of different condition and different body weight, the levels should be adapted accordingly. It is understood that the average daily energy intake preferably is about 2000 kcal. The nutritional composition, which may be a complete food, can be in the form of multiple dosage units, e.g. from 4 (e.g. 250 ml/unit) to 40 (e.g. 20 ml/unit) per day for an energy supply of 2000 kcal/day using the liquid enteral nutritional composition according to the invention.

The liquid enteral nutritional composition can also be a food supplement, for example to be used in addition to a non-medical food. Preferably as a supplement, the liquid enteral nutritional composition contains per daily dosage less than 1500 kcal; in particular as a supplement, the liquid enteral nutritional composition contains 400 to 1000 kcal per daily dose. The food supplement can be in the form of multiple dosage units, e.g. from 2 (250 ml/unit) to 10 (50 ml/unit) per day for an energy supply of 1000 kcal/day using the liquid enteral nutritional composition according to the invention.

In a further embodiment of the present invention, a unit dosage comprises any amount of the liquid enteral nutritional composition according to the invention between 10 ml and 250 ml, the end values of this range included, preferably any amount between 25 ml and 200 ml, the end values of this range included, more preferably any amount between 50 ml and 150 ml, the end values of this range included, most preferably about 125 ml. For example, a person receiving 50 ml unit dosages can be given 10 unit dosages per day to provide nutritional support using the liquid enteral nutritional composition according to the invention. Alternatively a person receiving 125 ml unit dosages can be given 4 or 5 or 6 or 7 or 8 unit dosages per day to provide nutritional support using the liquid enteral nutritional composition according to the invention. Such small dosage units are preferred because of better compliance.

In a further embodiment, the nutritional composition is administered as 1 to 2 servings daily, each serving comprising between 80 and 200 kcal, preferably about 125 kcal, preferably about 150 kcal. Preferably, the nutritional composition is administered as one serving daily. Using a nutritional composition in a liquid or spoonable form, the serving may comprise 30 to 250 ml of nutritional composition according to the invention, most preferably 200 ml per serving.

In a further embodiment of the present invention, the composition is provided in a ready to use liquid form and does not require reconstitution or mixing prior to use. The composition according to the invention can be tube fed or administered orally. For example, the composition according to the invention can be provided in a can, on spike, and hang bag.

In a further embodiment of the present invention, the composition according to the invention is packaged. The packaging may have any suitable form, for example a block-shaped carton, e.g. to be emptied with a straw; a carton or plastic beaker with removable cover; a small-sized bottle for example for the 80 ml to 200 ml range, and small cups for example for the 10 ml to 30 ml range. Another suitable packaging mode is inclusion of small volumes of liquid (e.g. 10 ml to 20 ml) in edible solid or semi-solid hulls or capsules, for example gelatine-like coverings and the like.

The invention will now be described by way of examples; these are not meant to be limiting.

EXPERIMENTAL

Example 1: According to the invention
Example 2: According to the invention
Example 3: According to Example 1 with about 130 mg/100 ml divalent metal cations
Example 4: According to Example 1 with 100 weight % non-acidified WPI.
Example 5: According to Example 1 with 40 weight % acidified and 60 weight % non-acidified WPI
Example 6: According to Example 1 with 116 g/L whey and 400 mg/100 ml Ca
Example 7: According to Example 1 with 160 g/L whey and 400 mg/100 ml Ca
Example 8: According to Example 1 with higher amounts of fat.
Example 9: According to Example 1 with pH=3.7 during DSI.
Example 10: According to Example 1 with pH=4.9 during DSI.
Example 11: (using a reference method, comparative to Example 1 but with homogenisation after DSI treatment
Example 12: (using a reference method, comparative to Example 1 but without DSI treatment)
Example 13: (Comparative, as Example 1 except for a divalent cations concentration of less than 100 mg/100 ml)
Example 14: according to the invention (spoonable product)
Example 15: according to the invention (spoonable product):

Example 1

To obtain 20 L final product 909 g WPI and 1412 g pre-acidified WPI were dissolved to dissolve a total amount of 2000 g whey protein in 12.7 kg demineralized water. This mixture was mixed under gentle stirring to avoid excessive foam formation. In this mixture also 8 g carotenoid mixture, 79 g L-leucine, 6 g L-isoleucine, 23 g L-valine, 280 g GOS syrup (45% w/w pure), 14 g Inulin fibre source (97% w/w pure), 31 g low viscosity pectin source (90% w/w pure), 60 g high methoxy pectin source (35% w/w pure) and 505 g sucrose were dissolved. The mixture was stirred for about 2 hours at ambient temperature until all macro nutrients were dissolved or evenly dispersed. 91 g calcium hydroxide was added to 1346 g demineralized water and stirred with a stirring rod for 5 minutes. 173 g citric acid monohydrate was added to the calcium hydroxide solution and after that the mixture is stirred again for 5 minutes at ambient temperature. 7 g choline chloride, 6 g sodium ascorbate, 9 g potassium chloride, 11 g tri-potassium citrate 1 aq, 30 g magnesium chloride 2 aq and 34 g tri-sodium citrate 2 aq were added to 492 g demineralized water and stirred for about 1 hour at ambient temperature until all minerals were dissolved or evenly dispersed. The solution containing the macro ingredients was mixed with the solution containing calcium hydroxide and with the solution containing the other minerals. This combined solution was stirred for several minutes to ensure evenly distribution of all components in the solution. The pH of this solution was set at pH 4.3 using lactic acid quantum satis. The pH was measured at ambient temperature with an electrode directly in the solution. 19 g soy lecithin and 278 g rapeseed oil were mixed at ambient temperature and subsequently heated until 60° C. in a water bath. The oil mixture was added to the previous solution. A pre-emulsion was formed by mixing the oil trough the solution using an ultra thurrax. The newly formed mixture was homogenized at 60° C. with 550+50 bar and cooled to ambient temperature. The emulsion was preheated until 60° C., heated using DSI to 115° C. for 4 seconds and flash cooled to 60° C. The emulsion was cooled until ambient temperature. After this treatment the pH of the emulsion was adjusted to 4.0 using lactic acid quantum satis. The pH was measured at ambient temperature with an electrode directly in the solution. The dry matter of the product was adjusted by adding demineralized water to obtain the required final dry matter. The emulsion was mixed for about 5 minutes to evenly distribute the water and the emulsion. The emulsion was pre-heated to 60° C. using a plate heat exchanger and given an UHT treatment. Product was filled in bottles in a sterile cabinet.

Example 2

To obtain 20 L final product 909 g WPI and 1412 g pre-acidified WPI were dissolved to dissolve a total amount of 2000 g whey protein in 11.7 kg tap water. This mixture was mixed under gentle stirring to avoid excessive foam formation. In this mixture also 79 g L-leucine, 6 g L-isoleucine, 23 g L-valine, 280 g GOS syrup (45% w/w pure) and 14 g Inulin fibre source (97% w/w pure) were dissolved. The mixture was stirred for about 2 hours at ambient temperature until all macro nutrients were dissolved or evenly dispersed. 8 g carotenoid mixture was dissolved in 75 g tap water, stirred for 5 minutes at ambient temperature and added to the macro nutrient mixture. 85 g calcium hydroxide was added to 1255 g tap water and stirred with a stirring rod for 1 minute. 161 g citric acid monohydrate was added to the calcium hydroxide solution and after that the mixture is stirred again for 3 minutes at ambient temperature. 7 g choline chloride, 8 g calcium chloride 2 aq, 24 g tri-potassium citrate 1 aq, 29 g magnesium chloride 2 aq and 30 g tri-sodium citrate 2 aq were added to 490 g tap water and stirred for about 1 hour at ambient temperature until all minerals were dissolved or evenly dispersed. 5 g mineral premix and 5 g tri-sodium citrate 2 aq were added to 90 g tap water and stirred for about 1 hour at ambient temperature until all minerals were dissolved or evenly dispersed. The solution containing the macro ingredients was mixed with the solution containing calcium hydroxide and with the other two mineral containing solutions. This combined solution was stirred for several minutes to ensure evenly distribution of all components in the solution. 45 g low viscosity pectin source (90% w/w pure), 80 g high methoxy pectin source (35% w/w pure) and 430 g sucrose are dry blended and added to the above described solution under gentle stirring at ambient temperature. The pH of this solution was set at pH 4.3 using lactic acid quantum satis. The pH was measured at ambient temperature with an electrode directly in the solution. 19 g soy lecithin and 278 g rapeseed oil were mixed at ambient temperature and subsequently heated until 60° C. in a water bath. The oil mixture was added to the previous solution. A pre-emulsion was formed by mixing the oil trough the solution using an ultra thurrax. The newly formed mixture was homogenized at 60° C. with 550+50 bar. The emulsion was preheated until 60° C., heated using DSI to 110° C. for 4 seconds and flash cooled to 60° C. The emulsion was cooled until ambient temperature. After this treatment the pH of the emulsion was adjusted to 4.0 using lactic acid quantum satis. The pH was measured at ambient temperature with an electrode directly in the solution. The dry matter of the product was adjusted by adding tap water to obtain the required final dry matter. The emulsion was mixed for about 5 minutes to evenly distribute the water and the emulsion. 5 g sodium ascorbate was added to the emulsion under gentle stirring. The emulsion was pre-heated to 60° C. using a tube heat exchanger and given an UHT treatment. Product was filled in bottles in a sterile cabinet.

Example 3

Example 1 with about 130 mg/100 ml Divalent Metal Cations

To obtain 20 L final product 909 g WPI and 1412 g pre-acidified WPI were dissolved to dissolve a total amount of 2000 g whey protein in 12.7 kg demineralized water. Before addition of the proteins, 8 g caroteinoid mixture was added to the water. This mixture was mixed under gentle stirring to avoid excessive foam formation. In this mixture also 79 g L-leucine, 6 g L-isoleucine, 23 g L-valine, 280 g GOS syrup (45% w/w pure), 15 g Inulin fibre source (97% w/w pure), 31 g low viscosity pectin source (90% w/w pure), 60 g high methoxy pectin source (35% w/w pure) and 505 g sucrose were dissolved. The mixture was stirred for about 2 hours at ambient temperature until all macro nutrients were dissolved or evenly dispersed. 46 g calcium hydroxide was added to 673 g demineralized water and stirred with a stirring rod for 5 minutes. 86 g citric acid monohydrate was added to the calcium hydroxide solution and after that the mixture is stirred again for 5 minutes at ambient temperature. 7 g choline chloride, 6 g sodium ascorbate, 9 g potassium chloride, 6 g tri-potassium citrate 1 aq, 15 g magnesium chloride 2 aq and 17 g tri-sodium citrate 2 aq were added to 256 g demineralized water and stirred for about 1 hour at ambient temperature until all minerals were dissolved or evenly dispersed. The solution containing the macro ingredients was mixed with the solution containing calcium hydroxide and with the solution containing the other minerals. This combined solution was stirred for several minutes to ensure evenly distribution of all components in the solution. The pH of this solution was set at pH 4.3 using lactic acid quantum satis. The pH was measured at ambient temperature with an electrode directly in the solution. 19 g soy lecithin and 278 g rapeseed oil were mixed at ambient temperature and subsequently heated until 60° C. in a water bath. The oil mixture was added to the previous solution. A pre-emulsion was formed by mixing the oil trough the solution using an ultra thurrax. The newly formed mixture was homogenized at 60° C. with 550+50 bar and cooled to ambient temperature. The emulsion was preheated until 60° C., heated using DSI to 115° C. for 4 seconds and flash cooled to 60° C. The emulsion was cooled until ambient temperature. After this treatment the pH of the emulsion was adjusted to 4.0 using lactic acid quantum satis. The pH was measured at ambient temperature with an electrode directly in the solution. The dry matter of the product was adjusted by adding demineralized water to obtain the required final dry matter. The emulsion was mixed for about 5 minutes to evenly distribute the water and the emulsion. The emulsion was pre-heated to 60° C. using a plate heat exchanger and given an UHT treatment. Product was filled in bottles in a sterile cabinet.

Example 4

Example 1 with 100 Weight % Non-Acidified WPI

To obtain 20 L final product 2273 g WPI was dissolved to dissolve a total amount of 2000 g whey protein in 12.7 kg demineralized water. This mixture was mixed under gentle stirring to avoid excessive foam formation. In this mixture also 79 g L-leucine, 6 g L-isoleucine, 23 g L-valine, 280 g GOS syrup (45% w/w pure), 15 g Inulin fibre source (97% w/w pure), 31 g low viscosity pectin source (90% w/w pure), 80 g high methoxy pectin source (35% w/w pure) and 505 g sucrose were dissolved. The mixture was stirred for about 2 hours at ambient temperature until all macro nutrients were dissolved or evenly dispersed. 49 g calcium hydroxide was added to 715 g demineralized water and stirred with a stirring rod for 5 minutes. 92 g citric acid monohydrate was added to the calcium hydroxide solution and after that the mixture is stirred again for 5 minutes at ambient temperature. 7 g choline chloride, 6 g sodium ascorbate, 11 g tri-sodium citrate 2 aq, 26 g magnesium hydrogen phosphate 3 aq, 35 g penta calcium triphosphate and 32 g calcium chloride were added to 583 g demineralized water and stirred for about 1 hour at ambient temperature until all minerals were dissolved or evenly dispersed. The solution containing the macro ingredients was mixed with the solution containing calcium hydroxide and with the solution containing the other minerals. This combined solution was stirred for several minutes to ensure evenly distribution of all components in the solution. The pH of this solution was set at pH 4.9 using lactic acid quantum satin. The pH was measured at ambient temperature with an electrode directly in the solution. 19 g soy lecithin and 278 g rapeseed oil were mixed at ambient temperature and subsequently heated until 60° C. in a water bath. The oil mixture was added to the previous solution. A pre-emulsion was formed by mixing the oil trough the solution using an ultra thurrax. The newly formed mixture was homogenized at 60° C. with 550+50 bar and cooled to ambient temperature. The emulsion was preheated until 60° C., heated using DSI to 110° C. for 4 seconds and flash cooled to 60° C. The emulsion was cooled until ambient temperature. After this treatment the pH of the emulsion was adjusted to 4.0 using lactic acid quantum satis. The pH was measured at ambient temperature with an electrode directly in the solution. The dry matter of the product was adjusted by adding demineralized water to obtain the required final dry matter. The emulsion was mixed for about 5 minutes to evenly distribute the water and the emulsion. The emulsion was pre-heated to 60° C. using a plate heat exchanger and given an UHT treatment. Product was filled in bottles in a sterile cabinet.

Example 5

Example 1 with 40 Weight % Acidified and 60 Weight % Non-Acidified WPI

To obtain 20 L final product 1364 g WPI and 941 g pre-acidified WPI were dissolved to dissolve a total amount of 2000 g whey protein in 12.6 kg demineralized water. This mixture was mixed under gentle stirring to avoid excessive foam formation. In this mixture also 79 g L-leucine, 6 g L-isoleucine, 23 g L-valine, 280 g GOS syrup (45% w/w pure), 15 g Inulin fibre source (97% w/w pure), 31 g low viscosity pectin source (90% w/w pure), 80 g high methoxy pectin source (35% w/w pure) and 505 g sucrose were dissolved. The mixture was stirred for about 2 hours at ambient temperature until all macro nutrients were dissolved or evenly dispersed. 86 g calcium hydroxide was added to 1265 g demineralized water and stirred with a stirring rod for 5 minutes. 162 g citric acid monohydrate was added to the calcium hydroxide solution and after that the mixture is stirred again for 5 minutes at ambient temperature. 7 g choline chloride, 6 g sodium ascorbate, 9 g tri potassium citrate 1 aq, 30 g magnesium chloride 6 aq, 25 g tri sodium citrate and 25 g calcium chloride were added to 438 g demineralized water and stirred for about 1 hour at ambient temperature until all minerals were dissolved or evenly dispersed. The solution containing the macro ingredients was mixed with the solution containing calcium hydroxide and with the solution containing the other minerals. This combined solution was stirred for several minutes to ensure evenly distribution of all components in the solution. The pH of this solution was set at pH 4.9 using lactic acid quantum satis. The pH was measured at ambient temperature with an electrode directly in the solution. 19 g soy lecithin and 278 g rapeseed oil were mixed at ambient temperature and subsequently heated until 60° C. in a water bath. The oil mixture was added to the previous solution. A pre-emulsion was formed by mixing the oil trough the solution using an ultra thurrax. The newly formed mixture was homogenized at 60° C. with 550+50 bar and cooled to ambient temperature. The emulsion was preheated until 60° C., heated using DSI to 110° C. for 4 seconds and flash cooled to 60° C. The emulsion was cooled until ambient temperature. After this treatment the pH of the emulsion was adjusted to 4.0 using lactic acid quantum satin. The pH was measured at ambient temperature with an electrode directly in the solution. The dry matter of the product was adjusted by adding demineralized water to obtain the required final dry matter. The emulsion was mixed for about 5 minutes to evenly distribute the water and the emulsion. The emulsion was pre-heated to 60° C. using a plate heat exchanger and given an UHT treatment. Product was filled in bottles in a sterile cabinet.

Example 6

Example 1 with 116 g/L Whey and 400 mg/100 ml Ca

To obtain 20 L final product 1055 g WPI and 1638 g pre-acidified WPI were dissolved to dissolve a total amount of 2320 g whey protein in 12.1 kg demineralized water. This mixture was mixed under gentle stirring to avoid excessive foam formation. In this mixture also 8 g carotenoid mixture, 216 g L-leucine, 444 g GOS syrup (45% w/w pure), 23 g Inulin fibre source (97% w/w pure), 49 g low viscosity pectin source (90% w/w pure), 60 g high methoxy pectin source (35% w/w pure) and 1088 g sucrose were dissolved. The mixture was stirred for about 2 hours at ambient temperature until all macro nutrients were dissolved or evenly dispersed. 149 g calcium hydroxide was added to 2191 g demineralized water and stirred with a stirring rod for 5 minutes. 281 g citric acid monohydrate was added to the calcium hydroxide solution and after that the mixture is stirred again for 5 minutes at ambient temperature. 12 g choline chloride, 9 g sodium ascorbate, 42 g magnesium hydrogen phosphate 2 aq, 33 g sodium chloride and 33 g di-potassium hydrogenphosphate were added to 641 g demineralized water and stirred for about 1 hour at ambient temperature until all minerals were dissolved or evenly dispersed. The solution containing the macro ingredients was mixed with the solution containing calcium hydroxide and with the solution containing the other minerals. This combined solution was stirred for several minutes to ensure evenly distribution of all components in the solution. The pH of this solution was set at pH 4.3 using lactic acid quantum satis. The pH was measured at ambient temperature with an electrode directly in the solution. 25 g soy lecithin and 372 g rapeseed oil were mixed at ambient temperature and subsequently heated until 60° C. in a water bath. The oil mixture was added to the previous solution. A pre-emulsion was formed by mixing the oil trough the solution using an ultra thurrax. The newly formed mixture was homogenized at 60° C. with 550+50 bar and cooled to ambient temperature. The emulsion was preheated until 60° C., heated using DSI to 115° C. for 4 seconds and flash cooled to 60° C. The emulsion was cooled until ambient temperature. After this treatment the pH of the emulsion was adjusted to 4.0 using lactic acid quantum satis. The pH was measured at ambient temperature with an electrode directly in the solution. The dry matter of the product was adjusted by adding demineralized water to obtain the required final dry matter. The emulsion was mixed for about 5 minutes to evenly distribute the water and the emulsion. The emulsion was pre-heated to 60° C. using a plate heat exchanger and given an UHT treatment. Product was filled in bottles in a sterile cabinet.

Example 7

Example 1 with 160 g/L Whey and 400 mg/100 ml Ca

To obtain 20 L final product 3546 g WPI was dissolved to dissolve a total amount of 3200 g whey protein in 13.0 kg demineralized water. This mixture was mixed under gentle stirring to avoid excessive foam formation. In this mixture also 80 g L-leucine, 18 g L-isoleucine, 10 g L-valine, 444 g GOS syrup (45% w/w pure) and 23 g Inulin fibre source (97% w/w pure) were dissolved. After all ingredients were dissolved or evenly dispersed the following ingredients were dissolved in this mixture: 51 g low viscosity pectin source (90% w/w pure), 80 g high methoxy pectin source (35% w/w pure) and 963 g sucrose. The mixture was stirred for about 2 hours at ambient temperature until all macro nutrients were dissolved or evenly dispersed. 82 g calcium hydroxide was added to 1210 g demineralized water and stirred with a stirring rod for 5 minutes. 155 g citric acid monohydrate was added to the calcium hydroxide solution and after that the mixture is stirred again for 5 minutes at ambient temperature. 12 g choline chloride, 9 g sodium ascorbate, 36 g magnesium hydrogen phosphate 2 aq, 42 g penta calcium triphosphate, 5 g potassium chloride and 10 g tri-potassium citrate 1 aq were added to 825 g demineralized water and stirred for about 1 hour at ambient temperature until all minerals were dissolved or evenly dispersed. The solution containing the macro ingredients was mixed with the solution containing calcium hydroxide and with the solution containing the other minerals. This combined solution was stirred for several minutes to ensure evenly distribution of all components in the solution. The pH of this solution was set at pH 4.3 using lactic acid quantum satis. The pH was measured at ambient temperature with an electrode directly in the solution. 30 g soy lecithin and 442 g rapeseed oil were mixed at ambient temperature and subsequently heated until 60° C. in a water bath. The oil mixture was added to the previous solution. A pre-emulsion was formed by mixing the oil trough the solution using an ultra thurrax. The newly formed mixture was homogenized at 20° C. with 550+50 bar and cooled to ambient temperature. The emulsion was heated using DSI to 115° C. for 4 seconds and flash cooled to 60° C. The emulsion was cooled until ambient temperature. After this treatment the pH of the emulsion was adjusted to 4.0 using lactic acid quantum satis. The pH was measured at ambient temperature with an electrode directly in the solution. The dry matter of the product was adjusted by adding demineralized water to obtain the required final dry matter. The emulsion was mixed for about 5 minutes to evenly distribute the water and the emulsion. The emulsion was pre-heated to 60° C. using a plate heat exchanger and given an UHT treatment. Product was filled in bottles in a sterile cabinet.

Example 8

Example 1 with Higher Amounts of Fat

To obtain 20 L final product 909 g WPI and 1412 g pre-acidified WPI were dissolved to dissolve a total amount of 2000 g whey protein in 12.7 kg demineralized water. This mixture was mixed under gentle stirring to avoid excessive foam formation. In this mixture also 8 g carotenoid mixture, 79 g L-leucine, 6 g L-isoleucine, 23 g L-valine, 280 g GOS syrup (45% w/w pure), 14 g Inulin fibre source (97% w/w pure), 31 g low viscosity pectin source (90% w/w pure), 60 g high methoxy pectin source (35% w/w pure) and 2738 g sucrose were dissolved. The mixture was stirred for about 2 hours at ambient temperature until all macro nutrients were dissolved or evenly dispersed. 91 g calcium hydroxide was added to 1346 g demineralized water and stirred with a stirring rod for 5 minutes. 173 g citric acid monohydrate was added to the calcium hydroxide solution and after that the mixture is stirred again for 5 minutes at ambient temperature. 7 g choline chloride, 6 g sodium ascorbate, 9 g potassium chloride, 11 g tri-potassium citrate 1 aq, 30 g magnesium chloride 2 aq and 34 g tri-sodium citrate 2 aq were added to 492 g demineralized water and stirred for about 1 hour at ambient temperature until all minerals were dissolved or evenly dispersed. The solution containing the macro ingredients was mixed with the solution containing calcium hydroxide and with the solution containing the other minerals. This combined solution was stirred for several minutes to ensure evenly distribution of all components in the solution. The pH of this solution was set at pH 4.3 using lactic acid quantum satis. The pH was measured at ambient temperature with an electrode directly in the solution. 80 g soy lecithin and 1120 g rapeseed oil were mixed at ambient temperature and subsequently heated until 60° C. in a water bath. The oil mixture was added to the previous solution. A pre-emulsion was formed by mixing the oil trough the solution using an ultra thurrax. The newly formed mixture was homogenized at 60° C. with 550+50 bar and cooled to ambient temperature. The emulsion was preheated until 60° C., heated using DSI to 115° C. for 4 seconds and flash cooled to 60° C. The emulsion was cooled until ambient temperature. After this treatment the pH of the emulsion was adjusted to 4.0 using lactic acid quantum satis. The pH was measured at ambient temperature with an electrode directly in the solution. The dry matter of the product was adjusted by adding demineralized water to obtain the required final dry matter. The emulsion was mixed for about 5 minutes to evenly distribute the water and the emulsion. The emulsion was pre-heated to 60° C. using a plate heat exchanger and given an UHT treatment. Product was filled in bottles in a sterile cabinet.

Example 9

Example 1 with pH=3.7 During DSI

To obtain 20 L final product 909 g WPI and 1412 g pre-acidified WPI were dissolved to dissolve a total amount of 2000 g whey protein in 13.5 kg demineralized water. This mixture was mixed under gentle stirring to avoid excessive foam formation. In this mixture also 8 g carotenoid mixture, 79 g L-leucine, 6 g L-isoleucine, 23 g L-valine, 280 g GOS syrup (45% w/w pure), 14 g Inulin fibre source (97% w/w pure), 31 g low viscosity pectin source (90% w/w pure), 60 g high methoxy pectin source (35% w/w pure) and 505 g sucrose were dissolved. The mixture was stirred for about 2 hours at ambient temperature until all macro nutrients were dissolved or evenly dispersed. 91 g calcium hydroxide was added to 1346 g demineralized water and stirred with a stirring rod for 5 minutes. 173 g citric acid monohydrate was added to the calcium hydroxide solution and after that the mixture is stirred again for 5 minutes at ambient temperature. 7 g choline chloride, 6 g sodium ascorbate, 9 g potassium chloride, 11 g tri-potassium citrate 1 aq, 30 g magnesium chloride 2 aq and 34 g tri-sodium citrate 2 aq were added to 492 g demineralized water and stirred for about 1 hour at ambient temperature until all minerals were dissolved or evenly dispersed. The solution containing the macro ingredients was mixed with the solution containing calcium hydroxide and with the solution containing the other minerals. This combined solution was stirred for several minutes to ensure evenly distribution of all components in the solution. The pH of this solution was set at pH 3.7 using lactic acid quantum satis. The pH was measured at ambient temperature with an electrode directly in the solution. 19 g soy lecithin and 278 g rapeseed oil were mixed at ambient temperature and subsequently heated until 60° C. in a water bath. The oil mixture was added to the previous solution. A pre-emulsion was formed by mixing the oil trough the solution using an ultra thurrax. The newly formed mixture was homogenized at 60° C. with 550+50 bar and cooled to ambient temperature. The emulsion was preheated until 60° C., heated using DSI to 115° C. for 4 seconds and flash cooled to 60° C. The emulsion was cooled until ambient temperature. After this treatment the pH of the emulsion was adjusted to 4.0 using a potassium hydroxide solution quantum satis. The pH was measured at ambient temperature with an electrode directly in the solution. The dry matter of the product was adjusted by adding demineralized water to obtain the required final dry matter. The emulsion was mixed for about 5 minutes to evenly distribute the water and the emulsion. The emulsion was pre-heated to 60° C. using a plate heat exchanger and given an UHT treatment. Product was filled in bottles in a sterile cabinet.

Example 10

Example 1 with pH=4.9 During DSI

To obtain 20 L final product 909 g WPI and 1412 g pre-acidified WPI were dissolved to dissolve a total amount of 2000 g whey protein in 13.5 kg demineralized water. This mixture was mixed under gentle stirring to avoid excessive foam formation. In this mixture also 8 g carotenoid mixture, 79 g L-leucine, 6 g L-isoleucine, 23 g L-valine, 280 g GOS syrup (45% w/w pure), 14 g Inulin fibre source (97% w/w pure), 31 g low viscosity pectin source (90% w/w pure), 60 g high methoxy pectin source (35% w/w pure) and 505 g sucrose were dissolved. The mixture was stirred for about 2 hours at ambient temperature until all macro nutrients were dissolved or evenly dispersed. 91 g calcium hydroxide was added to 1346 g demineralized water and stirred with a stirring rod for 5 minutes. 173 g citric acid monohydrate was added to the calcium hydroxide solution and after that the mixture is stirred again for 5 minutes at ambient temperature. 7 g choline chloride, 6 g sodium ascorbate, 9 g potassium chloride, 11 g tri-potassium citrate 1 aq, 30 g magnesium chloride 2 aq and 34 g tri-sodium citrate 2 aq were added to 492 g demineralized water and stirred for about 1 hour at ambient temperature until all minerals were dissolved or evenly dispersed. The solution containing the macro ingredients was mixed with the solution containing calcium hydroxide and with the solution containing the other minerals. This combined solution was stirred for several minutes to ensure evenly distribution of all components in the solution. The pH of this solution was set at pH 4.9 using a potassium hydroxide solution quantum satis. The pH was measured at ambient temperature with an electrode directly in the solution. 19 g soy lecithin and 278 g rapeseed oil were mixed at ambient temperature and subsequently heated until 60° C. in a water bath. The oil mixture was added to the previous solution. A pre-emulsion was formed by mixing the oil trough the solution using an ultra thurrax. The newly formed mixture was homogenized at 60° C. with 550+50 bar and cooled to ambient temperature. The emulsion was preheated until 60° C., heated using DSI to 115° C. for 4 seconds and flash cooled to 60° C. The emulsion was cooled until ambient temperature. After this treatment the pH of the emulsion was adjusted to 4.0 using lactic acid quantum satis. The pH was measured at ambient temperature with an electrode directly in the solution. The dry matter of the product was adjusted by adding demineralized water to obtain the required final dry matter. The emulsion was mixed for about 5 minutes to evenly distribute the water and the emulsion. The emulsion was pre-heated to 60° C. using a plate heat exchanger and given an UHT treatment. Product was filled in bottles in a sterile cabinet.

The results are summarized in Table 1.

TABLE 1

Summary of experiments

| | Example | | | | | | | | | |
|---|---|---|---|---|---|---|---|---|---|---|
| | 1 | 2 | 3 | 4 | 5 | 6 | 7 | 8 | 9 | 10 |
| Experiment code | 79.1 | ZM36.1 | 78.2 | 59.1 | 59.3 | 1.4 | 72.1 | 81.5 | 106.1 | 106.5 |
| Whey protein (g/100 ml) | 10 | 10 | 10 | 10 | 10 | 11.6 | 16 | 10 | 10 | 10 |

TABLE 1-continued

Summary of experiments

| | Example | | | | | | | | | |
|---|---|---|---|---|---|---|---|---|---|---|
| | 1 | 2 | 3 | 4 | 5 | 6 | 7 | 8 | 9 | 10 |
| Ratio acidified: neutral WPI | 60:40 | 60:40 | 60:40 | 100:0 | 40:60 | 60:40 | 100:0 | 60:40 | 60:40 | 60:40 |
| Calcium (mg/100 ml) | 250 | 250 | 131 | 250 | 250 | 401 | 320 | 250 | 250 | 250 |
| Fat (g/100 ml) | 1.5 | 1.5 | 1.5 | 1.5 | 1.5 | 2.0 | 2.4 | 6.0 | 1.5 | 1.5 |
| Carbohydrates (g/100 ml) | 4.8 | 4.7 | 4.3 | 5.2 | 5.6 | 8.3 | 8.7 | 15.9 | 4.8 | 4.8 |
| Kcal/100 mL | 75 | 75 | 74 | 75 | 77 | 103 | 120 | 160 | 75 | 75 |
| Viscosity (mPa · s) | 38 | 31 | 36 | 40 | 39 | 57 | 47 | 189 | 25 | 19 |
| pH during DSI | 4 | 4 | 4 | 4 | 4 | 4 | 4 | 4 | 3.7 | 4.9 |
| Astringency | ++ | ++ | 0 | ++ | ++ | ++ | ++ | ++ | ++ | ++ |
| Sandiness | ++ | ++ | ++ | 0 | ++ | ++ | 0 | ++ | ++ | ++ |

Viscosity is measured at 20° C. at a shear rate of 100 s−1.
Astringency: low in astringency (++), astringent (0), very astringent (−−)
Sandiness: low in sandiness (++), sandy (0), very sandy (−−)

Example 11

As Example 1 with Homogenization after DSI Treatment

To obtain 20 L final product 909 g WPI and 1412 g pre-acidified WPI were dissolved to dissolve a total amount of 2000 g whey protein in 11.7 kg tap water. This mixture was mixed under gentle stirring to avoid excessive foam formation. In this mixture also 79 g L-leucine, 6 g L-isoleucine, 23 g L-valine, 280 g GOS syrup (45% w/w pure) and 14 g Inulin fibre source (97% w/w pure) were dissolved. The mixture was stirred for about 2 hours at ambient temperature until all macro nutrients were dissolved or evenly dispersed. 8 g carotenoid mixture was dissolved in 75 g tap water, stirred for 5 minutes at ambient temperature and added to the macro nutrient mixture. 85 g calcium hydroxide was added to 1255 g tap water and stirred with a stirring rod for 1 minute. 161 g citric acid monohydrate was added to the calcium hydroxide solution and after that the mixture is stirred again for 3 minutes at ambient temperature. 7 g choline chloride, 8 g calcium chloride 2 aq, 24 g tri-potassium citrate 1 aq, 29 g magnesium chloride 2 aq and 30 g tri-sodium citrate 2 aq were added to 490 g tap water and stirred for about 1 hour at ambient temperature until all minerals were dissolved or evenly dispersed. 5 g mineral premix and 5 g tri-sodium citrate 2 aq were added to 90 g tap water and stirred for about 1 hour at ambient temperature until all minerals were dissolved or evenly dispersed. The solution containing the macro ingredients was mixed with the solution containing calcium hydroxide and with the other two mineral containing solutions. This combined solution was stirred for several minutes to ensure evenly distribution of all components in the solution. 45 g low viscosity pectin source (90% w/w pure), 80 g high methoxy pectin source (35% w/w pure) and 430 g sucrose are dry blended and added to the above described solution under gentle stirring at ambient temperature. The pH of this solution was set at pH 4.3 using lactic acid quantum satis. The pH was measured at ambient temperature with an electrode directly in the solution. 19 g soy lecithin and 278 g rapeseed oil were mixed at ambient temperature and subsequently heated until 60° C. in a water bath. The oil mixture was added to the previous solution. A pre-emulsion was formed by mixing the oil trough the solution using an ultra thurrax. The newly formed mixture was preheated until 60° C., heated using DSI to 110° C. for 4 seconds, flash cooled to 60° C. and homogenized at 60° C. with 550+50 bar. The emulsion was cooled until ambient temperature. After this heat treatment the pH of the emulsion was adjusted to 4.0 using lactic acid quantum satis. The pH was measured at ambient temperature with an electrode directly in the solution. The dry matter of the product was adjusted by adding tap water to obtain the required final dry matter. The emulsion was mixed for about 5 minutes to evenly distribute the water and the emulsion. 5 g sodium ascorbate was added to the emulsion under gentle stirring. The emulsion was pre-heated to 60° C. using a tube heat exchanger and given an UHT treatment. Product was filled in bottles in a sterile cabinet.

Example 12

As Example 1 without DSI Treatment

To obtain 20 L final product 909 g WPI and 1412 g pre-acidified WPI were dissolved to dissolve a total amount of 2000 g whey protein in 12.7 kg demineralized water. This mixture was mixed under gentle stirring to avoid excessive foam formation. In this mixture also 8 g carotenoid mixture, 79 g L-leucine, 6 g L-isoleucine, 23 g L-valine, 280 g GOS syrup (45% w/w pure), 14 g Inulin fibre source (97% w/w pure), 31 g low viscosity pectin source (90% w/w pure), 60 g high methoxy pectin source (35% w/w pure) and 505 g sucrose were dissolved. The mixture was stirred for about 2 hours at ambient temperature until all macro nutrients were dissolved or evenly dispersed. 91 g calcium hydroxide was added to 1346 g demineralized water and stirred with a stirring rod for 5 minutes. 173 g citric acid monohydrate was added to the calcium hydroxide solution and after that the mixture is stirred again for 5 minutes at ambient temperature. 7 g choline chloride, 6 g sodium ascorbate, 9 g potassium chloride, 11 g tri-potassium citrate 1 aq, 30 g magnesium chloride 2 aq and 34 g tri-sodium citrate 2 aq were added to 492 g demineralized water and stirred for about 1 hour at ambient temperature until all minerals were dissolved or evenly dispersed. The solution containing the macro ingredients was mixed with the solution containing calcium hydroxide and with the solution containing the other minerals. This combined solution was stirred for several minutes to ensure evenly distribution of all components in the solution. The pH of this solution was set at pH 4.3 using lactic acid quantum satis. The pH was measured at ambient temperature with an electrode directly in the solution. 19 g soy lecithin and 278 g rapeseed oil were mixed at ambient temperature and subsequently heated until 60° C. in a water bath. The oil mixture was added to the previous solution. A pre-emulsion was formed by mixing the oil trough the solution using an ultra thurrax. The newly formed mixture was homogenized at 60° C. with 550+50 bar and cooled to ambient temperature. The pH of the emulsion was adjusted to 4.0 using lactic acid quantum satis. The pH was measured at ambient temperature with an electrode directly in the solution. The dry matter of the product was adjusted by adding demineralized water to obtain the required final dry matter. The emulsion was mixed for about 5 minutes to evenly distribute the water and the emulsion. The emulsion was pre-heated to 60° C. using a plate heat exchanger and given an UHT treatment. Product was filled in bottles in a sterile cabinet.

Example 13

Comparative, as Example 1, but with Less than 100 mg/100 ml Divalent Cations

To obtain 20 L final product 909 g WPI and 1412 g pre-acidified WPI were dissolved to dissolve a total amount of 2000 g whey protein in 12.7 kg demineralized water. Before addition of the proteins, 8 g caroteinoid mixture was added to the water. This mixture was mixed under gentle stirring to avoid excessive foam formation. In this mixture also 79 g L-leucine, 6 g L-isoleucine, 23 g L-valine, 280 g GOS syrup (45% w/w pure), 15 g Inulin fibre source (97% w/w pure), 31 g low viscosity pectin source (90% w/w pure), 60 g high methoxy pectin source (35% w/w pure) and 505 g sucrose were dissolved. The mixture was stirred for about 2 hours at ambient temperature until all macro nutrients were dissolved or evenly dispersed. The pH of this solution was set at pH 4.3 using lactic acid quantum satis. The pH was measured at ambient temperature with an electrode directly in the solution. 19 g soy lecithin and 278 g rapeseed oil were mixed at ambient temperature and subsequently heated until 60° C. in a water bath. The oil mixture was added to the previous solution. A pre-emulsion was formed by mixing the oil trough the solution using an ultra thurrax. The newly formed mixture was homogenized at 60° C. with 550+50 bar and cooled to ambient temperature. The emulsion was preheated until 60° C., heated using DSI to 115° C. for 4 seconds and flash cooled to 60° C. The emulsion was cooled until ambient temperature. After this treatment the pH of the emulsion was adjusted to 4.0 using lactic acid quantum satis. The pH was measured at ambient temperature with an electrode directly in the solution. The dry matter of the product was adjusted by adding demineralized water to obtain the required final dry matter. The emulsion was mixed for about 5 minutes to evenly distribute the water and the emulsion. The emulsion was pre-heated to 60° C. using a plate heat exchanger and given an UHT treatment. Product was filled in bottles in a sterile cabinet. The results are summarized in Table 2.

TABLE 2

Summary of Examples 11-13

| | Example | | |
|---|---|---|---|
| | Ex 11 (ref. method) | Ex12 (ref. method) | Ex 13 (comparative) |
| Experiment code | ZM36.2 | 79.2 | 78.1 |
| Whey protein (g/100 ml) | 10 | 10 | 10 |
| Ratio acidified:neutral whey | 60:40 | 60:40 | 60:40 |
| Calcium (mg/100 ml) | 250 | 250 | 12 |
| Fat (g/100 ml) | 1.5 | 1.5 | 1.5 |
| Carbohydrates (g/100 ml) | 4.4 | 4.8 | 3.8 |
| Kcal/100 mL | 75 | 75 | 72 |
| Viscosity (mPa · s) | 35 | 118 | 92 |
| Astringency | 0 | — | — |
| pH during DSI | 4 | no DSI | 4 |
| Sandiness | — | 0 | 0 |

Viscosity is measured at 20° C. at a shear rate of 100 s−1.
Astringency: low in astringency (++), astringent (0), very astringent (−−)
Sandiness: low in sandiness (++), sandy (0), very sandy (−−)

Example 14

Preparation of a Spoonable Composition

To obtain 20 L final product 909 g WPI and 1412 g pre-acidified WPI, giving a total amount of 2000 g whey protein, were dissolved in 12.6 kg demineralized water. This mixture was mixed under gentle stirring to avoid excessive foam formation. In this mixture also 8 g carotenoid mixture, 79 g L-leucine, 6 g L-isoleucine, 23 g L-valine, 280 g GOS syrup (45% w/w pure), 14 g Inulin fibre source (97% w/w pure), 31 g low viscosity pectin source (90% w/w pure), 200 g high methoxy pectin source (35% w/w pure) and 505 g sucrose were dissolved. The mixture was stirred for about 2 hours at ambient temperature until all macro nutrients were dissolved or evenly dispersed. 91 g calcium hydroxide was added to 1346 g demineralized water and stirred with a stirring rod for 5 minutes. 173 g citric acid monohydrate was added to the calcium hydroxide solution and after that the mixture is stirred again for 5 minutes at ambient temperature. 7 g choline chloride, 6 g sodium ascorbate, 9 g potassium chloride, 11 g tri-potassium citrate 1 aq, 30 g magnesium chloride 2 aq and 34 g tri-sodium citrate 2 aq were added to 492 g demineralized water and stirred for about 1 hour at ambient temperature until all minerals were dissolved or evenly dispersed. The solution containing the macro ingredients was mixed with the solution containing calcium hydroxide and with the solution containing the other minerals. This combined solution was stirred for several minutes to ensure evenly distribution of all components in the solution. The pH of this solution was set at pH 4.0 using lactic acid quantum satis. The pH was measured at ambient temperature with an electrode directly in the solution. 19 g soy lecithin and 278 g rapeseed oil were mixed at ambient temperature and subsequently heated until 60° C. in a water bath. The oil mixture was added to the previous solution. A pre-emulsion was formed by mixing the oil trough the solution using an ultra thurrax. The newly formed mixture was homogenized at 60° C. with 550+50 bar and cooled to ambient temperature. The emulsion was preheated until 60° C., heated using DSI to 115° C. for 4 seconds and flash cooled to 60° C. The emulsion was cooled until ambient temperature. After this treatment the pH of the emulsion was checked and if needed adjusted to 4.0 using lactic acid quantum satis. The pH was measured at ambient temperature with an electrode directly in the solution. The dry matter of the product was adjusted by adding demineralized water to obtain the required final dry matter. The emulsion was mixed for about 5 minutes to evenly distribute the water and the emulsion. The emulsion was pre-heated to 60° C. using a plate heat exchanger and given an UHT treatment. Product was filled in plastic cups in a sterile cabinet.

Example 15

Preparation of a Spoonable Composition

To obtain 20 L final product 909 g WPI and 1412 g pre-acidified WPI, giving a total amount of 2000 g whey protein, were dissolved in 12.5 kg demineralized water. This mixture was mixed under gentle stirring to avoid excessive foam formation. In this mixture also 8 g carotenoid mixture, 79 g L-leucine, 6 g L-isoleucine, 23 g L-valine, 280 g GOS syrup (45% w/w pure), 14 g Inulin fibre source (97% w/w pure), 31 g low viscosity pectin source (90% w/w pure), 60 g high methoxy pectin source (35% w/w pure), 200 g modified starch (E1442) and 505 g sucrose were dissolved. The mixture was stirred for about 2 hours at ambient temperature until all macro nutrients were dissolved or evenly dispersed. 91 g calcium hydroxide was added to 1346 g demineralized water and stirred with a stirring rod for 5 minutes. 173 g citric acid monohydrate was added to the calcium hydroxide solution and after that the mixture is stirred again for 5 minutes at ambient temperature. 7 g choline chloride, 6 g sodium ascorbate, 9 g potassium chloride, 11 g tri-potassium citrate 1 aq, 30 g magnesium chloride 2 aq and 34 g tri-sodium citrate 2 aq were added to 492 g demineralized water and stirred for about 1 hour at ambient temperature until all minerals were dissolved or evenly dispersed. The solution containing the macro ingredients was mixed with the solution containing calcium hydroxide and with the solution containing the other minerals. This combined solution was stirred for several minutes to ensure evenly distribution of all components in the solution. The pH of this solution was set at pH 4.0 using lactic acid quantum satis. The pH was measured at ambient temperature with an electrode directly in the solution. 19 g soy lecithin and 278 g rapeseed oil were mixed at ambient temperature and subsequently heated until 60° C. in a water bath. The oil mixture was added to the previous solution. A pre-emulsion was formed by mixing the oil trough the solution using an ultra thurrax. The newly formed mixture was homogenized at 60° C. with 550+50 bar and cooled to ambient temperature. The emulsion was preheated until 60° C., heated using DSI to 115° C. for 4 seconds and flash cooled to 60° C. The emulsion was cooled until ambient temperature. After this treatment the pH of the emulsion was checked and if needed adjusted to 4.0 using lactic acid quantum satis. The pH was measured at ambient temperature with an electrode directly in the solution. The dry matter of the product was adjusted by adding demineralized water to obtain the required final dry matter. The emulsion was mixed for about 5 minutes to evenly distribute the water and the emulsion. The emulsion was pre-heated to 60° C. using a plate heat exchanger and given an UHT treatment. Product was filled in plastic cups in a sterile cabinet.

|  | Example | |
| --- | --- | --- |
|  | 14 | 15 |
| Experiment code | 6.1 | 6.2 |
| Whey protein (g/100 ml) | 10 | 10 |
| Ratio acidified:neutral WPI | 40:60 | 40:60 |

-continued

|  | Example | |
| --- | --- | --- |
|  | 14 | 15 |
| Calcium (mg/100 ml) | 250 | 250 |
| Fat (g/ml) | 1.5 | 1.5 |
| Carbohydrates (g/ml) | 5.1 | 5.8 |
| Stabilizers | 0.35% HM pectin | 0.1% HM pectin 1% Starch |
| Kcal/100 mL | 77 | 79 |
| Viscosity (mPa · s) (time) | 308 (0 wk) 579 (6 wk) | 246 (0 wk) 490 (6 wk) |
| pH during DSI | 4 | 4 |
| Astringency | ++ | ++ |
| Sandiness | ++ | ++ |

2. Nutritional Compositions

The following nutritional composition according to the invention is suitable for the prevention or treatment of a disease in an elderly mammal, which involves muscle protein synthesis.

TABLE 3

Example of a liquid sip feed composition (200 ml Serving size)

| Ingredient | Liquid sip feed (per 100 kcal) | Liquid sip feed (per 100 ml) |
| --- | --- | --- |
| Energy (kcal) | 100 | 75 |
| protein (En %) | 56 | 56 |
| fat (En %) | 18 | 18 |
| digestible carb (En %) | 23 | 23 |
| indigestible carb (En %) | 3 | 3 |
| Total protein (g) | 14.0 | 10.5 |
| Intact whey protein (g) | 13.3 | 10.0 |
| (wt % of proteinaceous matter) | (95 wt %) | (95 wt %) |
| Free leucine (g) | 0.5 | 0.4 |
| (wt % of total leucine) | (26 wt %) | (26 wt %) |
| Total leucine (g) | 2.0 | 1.5 |
| (wt % of proteinaceous matter) | (14 wt %) | (14 wt %) |
| Total isoleucine (g) | 1.0 | 0.75 |
| Total valine (g) | 1.0 | 0.75 |
| EAA (g) | 7.0 | 5.3 |
| (wt % of proteinaceous matter) | (50 wt %) | (50 wt %) |
| Fat (g) | 2.0 | 1.5 |
| Digestible carbohydrates (g) | 6.4 | 4.8 |
| Indigestible carbohydrates (g) | 1.11 | 0.83 |
| GOS (g) | 0.83 | 0.63 |
| FOS/inulin (g) | 0.09 | 0.07 |
| Low-viscosity pectin (g) | 0.19 | 0.14 |
| Ca (mg) | 332 | 250 |
| Mg (mg) | 25 | 19 |
| Fe (mg) | 1.6 | 1.2 |
| Zn (mg) | 1.5 | 1.1 |
| Se (μg) | 10 | 7.5 |
| Carotenoids (μg) | 200 | 150 |
| Vitamin C (mg) | 21.3 | 16.0 |
| Vitamin E (mg-α-TE) | 5.0 | 3.8 |
| Vitamin D3 (μg) | 13.3 | 10.0 |
| Vitamin B6 (μg) | 500 | 375 |
| Folic acid (μg) | 133 | 100 |
| Vitamin B12 (μg) | 2.0 | 1.5 |
| pH | 4 | |

EXEMPLARY EMBODIMENTS OF THE PRESENT INVENTION

Embodiment (A)

A sterilized liquid acid enteral nutritional composition comprising per 100 ml of said composition 9 to 20 g of non-hydrolysed globular protein, fat, and at least 100 mg of divalent metal cations and having a pH ranging between 3 and 5.

Embodiment (B)

Nutritional composition according to the preceding embodiment, wherein the pH ranges between 3.7 and 4.3, preferably is equal to about 4.0.

Embodiment (C)

Nutritional composition according to any one of the preceding embodiments, wherein the amount of divalent metal cations ranges between 100 and 600 mg per 100 ml.

Embodiment (D)

Nutritional composition according to any one of the preceding embodiments, wherein the amount of non-hydrolysed globular protein ranges between 4 and 16 g, preferably is equal to about 10 g per 100 ml of the composition.

Embodiment (E)

Nutritional composition according to any one of the preceding embodiments, wherein the divalent metal cation is selected from the group consisting of Ca, Mg and any mixture thereof, preferably is Ca.

Embodiment (F)

Nutritional composition according to any one of the preceding embodiments, wherein the globular protein is selected from the group consisting of whey protein, pea protein, soy protein, and any mixture thereof.

Embodiment (G)

Nutritional composition according to embodiment 6, wherein the source of whey protein is selected from the group consisting of whey protein concentrate (WPC), whey protein isolate (WPI), and any mixture thereof.

Embodiment (H)

Nutritional composition according to any one of the preceding embodiments, wherein the amount of non-hydrolysed globular protein is at least 85 weight % of the total proteinaceous matter in the composition.

Embodiment (I)

Nutritional composition according to any one of the preceding embodiments, further comprising a non-globular protein, a hydrolysed protein, an oligopeptide, a peptide or a free amino acid.

Embodiment (J)

Nutritional composition according to embodiment 9, wherein the non-globular protein is selected from the group of casein, caseinate, micellar casein isolate, and any mixture thereof.

Embodiment (K)

Nutritional composition according to embodiment 9, wherein the free amino acid is selected from the group of branched chain amino acids, in particular is L-leucine.

Embodiment (L)

Nutritional composition according to any one of the preceding embodiments, said fat providing between 15 to 65% of the total energy amount of the composition.

Embodiment (M)

Nutritional composition according to any one of the preceding embodiments, further comprising carbohydrate, said carbohydrate providing between 20 to 60% of the total energy amount of the composition.

Embodiment (N)

Nutritional composition according to any one of the preceding embodiments, wherein the viscosity of the composition is lower than 200 mPa·s, preferably lower than 100 mPa·s, measured at 20° C. at a shear rate of 100 s$^{-1}$.

Embodiment (O)

Nutritional composition according to any one of the preceding embodiments, in a unit dosage container of about 200 ml.

Embodiment (P)

Nutritional composition according to any one of the preceding embodiments comprising:
a) about 10 g of non-hydrolysed whey per 100 ml of the composition, said protein providing about 56% of the total energy amount of the composition;
b) fat providing about 18% of the total energy amount of the composition;
c) optionally carbohydrate providing about 23% of the total energy amount of the composition,
d) about 250 mg per 100 ml of Ca and about 19 mg of Mg per 100 ml; and
e) having a pH of about 4.

Embodiment (Q)

The use of a nutritional composition according to any one of the preceding embodiments for the manufacture of a nutritionally complete food.

Embodiment (R)

Nutritional composition according to any one of the preceding embodiments, for use in nutritional management of a person in need thereof.

Embodiment (S)

Nutritional composition according to embodiment (R), wherein the person is an elderly person, a person that is in a disease state, a person that is recovering from a disease state, a person that is malnourished, a sportsman, or an active elderly.

Embodiment (T)

Nutritional composition according to embodiment (R) or (S) for the prevention or treatment of a disease or condition involving muscle decline in a mammal, in particular for treating sarcopenia.

Embodiment (U)

A method for the preparation of a sterilized liquid acid enteral composition comprising per 100 ml 9 to 20 g of non-hydrolysed globular proteins, fat and at least 100 mg of divalent metal cations and having a pH ranging between 3 and 5 according to any one of the embodiments (A) to (P), comprising a step wherein at least the non-hydrolysed globular proteins are subjected to a homogenization step, followed by direct steam injection (DSI) at specific holding values, such as a holding temperature of 100 to 140° C. during a holding time of about 0.5 to 10 seconds, followed by a sterilization step.

Embodiment (V)

Method according to embodiment (U), comprising the consecutive steps of:
a) preparing an aqueous solution comprising amounts of divalent metal cations, in particular calcium and magnesium, non-hydrolysed globular proteins and fat, such that said sterilized liquid acid enteral composition comprises per 100 ml of said composition 9 to 20 g of non-hydrolysed globular proteins, fat, and at least 100 mg of divalent metal cations, and having a pH ranging between 3 and 5;
b) homogenizing the resulting solution essentially obtained by step a);
c) subjecting the resulting solution essentially obtained by step b) to a direct steam injection process at a holding temperature of 100 to 140° C. during a holding time of about 0.5 to 10 seconds; and
d) subjecting the resulting solution essentially obtained by step c) to a sterilization treatment.

Embodiment (W)

Sterilized liquid acid enteral composition comprising per 100 ml 9 to 20 g of non-hydrolysed globular proteins, fat and at least 100 mg of divalent metal cations and having a pH ranging between 3 and 5, obtainable by a method according to embodiment (U) or (V).

The invention claimed is:

1. A method for the preparation of a sterilized liquid or semi-solid acid enteral composition comprising per 100 ml of said composition 9 to 20 g of non-hydrolysed globular protein, which globular protein is selected from the group consisting of whey protein, pea protein, and soy protein, and any mixture thereof, the composition further comprising fat, and at least 100 mg of divalent metal cations and having a pH ranging between 3 and 5, comprising a step wherein at least the non-hydrolysed globular proteins are subjected to a homogenization step, followed by direct steam injection (DSI) at a holding temperature of 100 to 140° C. during a holding time of about 0.5 to 10 seconds.

2. The method according to claim 1, wherein direct steam injection is followed by a sterilization step.

3. The method according to claim 1, wherein the enteral composition further comprises a stabilizing polysaccharide selected from the group consisting of high methoxy pectin, and carboxymethyl cellulose and combinations thereof, said process comprising the step wherein at least the non-hydrolysed whey proteins and said polysaccharide together are subjected to homogenization followed by direct steam injection (DSI).

4. The method according to claim 1, comprising the consecutive steps of
a) preparing an aqueous solution comprising amounts of divalent metal cations, non-hydrolysed globular proteins and fat, such that said sterilized liquid acid enteral composition comprises per 100 ml of said composition 9 to 20 g of non-hydrolysed globular proteins, fat, and at least 100 mg of divalent metal cations, and having a pH ranging between 3 and 5;
b) homogenizing the resulting solution essentially obtained by step a); and
c) subjecting the resulting solution obtained by step b) to a direct steam injection process at a holding temperature of 100 to 140° C. during a holding time of about 0.5 to 10 seconds.

5. The method according to claim 4, wherein step c) is followed by the step of d) subjecting the resulting solution obtained by step c) to a sterilization treatment.

6. The method according to claim 4, wherein the enteral composition further comprises a stabilizing polysaccharide selected from the group consisting of high methoxy pectin, and carboxymethyl cellulose and combinations thereof, said process comprising the step of a) preparing an aqueous solution comprising amounts of divalent metal cations, non-hydrolysed whey protein, fat and the polysaccharide.

7. The method according to claim 1 for the preparation of a semi-solid enteral nutritional composition, said method comprising the steps of adding a thickener or gelling agent to the sterilized liquid acid enteral composition and further processing the mixture into the final semi-solid product.

8. The method according to claim 1 for the preparation of a semi-solid enteral nutritional composition, said method comprising the steps of adding a thickener or gelling agent to the aqueous solution of step a).

9. The method of claim 1 wherein the pH is equal to about 4.0.

10. The method of claim 1 wherein the amount of non-hydrolysed globular protein is equal to about 10 g per 100 ml of the composition.

11. The method of claim 1 wherein the nutritional composition further includes free branched chain amino acid.

12. The method of claim 4 wherein the divalent metal cations are calcium or magnesium.

13. The method of claim 1 wherein the pH ranges between 3.7 and 4.3.

14. The method of claim 1 wherein the nutritional composition further comprises a stabilizing polysaccharide selected from the group consisting of (high) methoxy pectin and carboxymethyl cellulose and combinations thereof.

15. The method of claim 1 wherein the amount of divalent metal cations ranges between 100 and 600 mg per 100 ml.

16. The method of claim 1 wherein the amount of non-hydrolysed globular protein ranges between 9 and 16 g.

17. The method of claim 1 wherein the divalent metal cation is selected from the group consisting of Ca and Mg and any mixture thereof.

18. The method of claim 1 wherein the divalent metal cation is Ca.

19. The method of claim 1 wherein the globular protein comprises whey protein and the source of whey protein is selected from the group consisting of whey protein concentrate (WPC), whey protein isolate (WPI), and any mixture thereof.

20. The method of claim 1 wherein the amount of non-hydrolysed globular protein is at least 85 weight % of the total proteinaceous matter in the composition.

21. The method of claim 1 wherein the nutritional composition further includes free amino acid.

22. The method of claim 1 wherein the fat provides between 15 to 65% of the total energy amount of the composition.

23. The method of claim 1 wherein the nutritional composition further includes carbohydrate, said carbohydrate providing between 20 to 60% of the total energy amount of the composition.

24. The method of claim 1 wherein the composition is a liquid and the viscosity of the composition is lower than 100 mPa·s, measured at 20° C. at a shear rate of 100 s$^{-1}$.

* * * * *